US012728216B2

(12) United States Patent
Pocreva, III et al.

(10) Patent No.: US 12,728,216 B2
(45) **Date of Patent: *Sep. 8, 2026**

(54) APPARATUS, SYSTEM AND METHOD FOR DETECTING AND MONITORING INHALATIONS

(71) Applicant: MANNKIND CORPORATION, Valencia, CA (US)

(72) Inventors: John J. Pocreva, III, Lagrangeville, NY (US); Benoit Adamo, South Salem, NY (US); Brendan Laurenzi, Rutland, MA (US); Chad C. Smutney, Watertown, CT (US); P. Spencer Kinsey, Sandy Hook, CT (US)

(73) Assignee: MANNKIND CORPORATION, Valencia, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/931,098

(22) Filed: Sep. 9, 2022

(65) Prior Publication Data

US 2023/0001112 A1 Jan. 5, 2023

Related U.S. Application Data

(63) Continuation of application No. 16/301,700, filed as application No. PCT/US2017/033627 on May 19, 2017, now Pat. No. 11,478,591.

(Continued)

(51) Int. Cl.

*A61M 15/00* (2006.01)
*A61B 5/087* (2006.01)

(Continued)

(52) U.S. Cl.

CPC .......... *A61M 15/008* (2014.02); *A61K 38/28* (2013.01); *A61K 47/22* (2013.01);

(Continued)

(58) Field of Classification Search

CPC .......... A61K 38/28; A61K 47/22; G09B 5/02; G09B 23/28

See application file for complete search history.

(56) References Cited

U.S. PATENT DOCUMENTS 5,392,768 A * 2/1995 Johansson ............ G01F 13/006 128/200.14
5,469,750 A 11/1995 Lloyd et al.

(Continued)

FOREIGN PATENT DOCUMENTS

DE 102008051515 A1 4/2010
EP 0469797 A1 2/1992

(Continued)

OTHER PUBLICATIONS

Office Action issued in corresponding Australian Application No. 2022203725, dated Dec. 7, 2023, 6 pages.

(Continued)

*Primary Examiner* — Joseph D. Boecker
*Assistant Examiner* — Thomas W Greig
(74) *Attorney, Agent, or Firm* — Morgan, Lewis & Bockius LLP

(57) ABSTRACT

Described herein are an interactive apparatus and methods for sensing and measuring real-time characteristic patterns of a subject's use of a dry powder inhalation system. The inhaler device can be used in a wireless communication mode to communicate with a display to assess the subject's usage of the inhalation system concurrently as the inhalation is performed and thus the subject's inhalation can be evaluated as well as the performance of the inhalation system. The system can also detect the identity of the medicament, its dosage, lot, expiration, etc. and the characteristics profile of a dry powder formulation emitted from the inhalation system in use.

25 Claims, 12 Drawing Sheets

Related U.S. Application Data

(60) Provisional application No. 62/338,971, filed on May 19, 2016.

(51) Int. Cl.

| | |
|---|---|
| ***A61K 38/28*** | (2006.01) |
| ***A61K 47/22*** | (2006.01) |
| ***A61M 16/00*** | (2006.01) |
| ***A61M 16/16*** | (2006.01) |
| ***G09B 5/02*** | (2006.01) |
| ***G09B 23/28*** | (2006.01) |

(52) U.S. Cl.

CPC .... *A61M 15/0028* (2013.01); *A61M 15/0065* (2013.01); *G09B 5/02* (2013.01); *G09B 23/28* (2013.01); *A61B 5/087* (2013.01); *A61B 2562/08* (2013.01); *A61M 15/0021* (2014.02); *A61M 15/0043* (2014.02); *A61M 2016/0021* (2013.01); *A61M 2016/0027* (2013.01); *A61M 2016/0033* (2013.01); *A61M 16/161* (2014.02); *A61M 2202/064* (2013.01); *A61M 2205/13* (2013.01); *A61M 2205/3306* (2013.01); *A61M 2205/3313* (2013.01); *A61M 2205/3331* (2013.01); *A61M 2205/3344* (2013.01); *A61M 2205/3358* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/583* (2013.01); *A61M 2205/587* (2013.01); *A61M 2205/6018* (2013.01); *A61M 2205/6054* (2013.01); *A61M 2205/6063* (2013.01); *A61M 2205/6081* (2013.01); *A61M 2205/8206* (2013.01); *A61M 2206/10* (2013.01); *A61M 2230/40* (2013.01)

(56) References Cited

U.S. PATENT DOCUMENTS

| | | | | |
|---|---|---|---|---|
| 5,497,764 | A | 3/1996 | Ritson et al. | |
| 5,794,612 | A | 8/1998 | Wachter et al. | |
| 6,328,033 | B1 | 12/2001 | Avrahami | |
| 6,651,651 | B1 | 11/2003 | Bonney et al. | |
| 6,752,145 | B1 * | 6/2004 | Bonney | A61M 15/009 128/200.23 |
| 8,807,131 | B1 * | 8/2014 | Tunnell | A61M 15/0021 128/200.14 |
| 9,869,600 | B2 * | 1/2018 | Haldorsen | G01L 13/025 |
| 2004/0187869 | A1 * | 9/2004 | Bjorndal | A61M 15/0065 128/200.23 |
| 2006/0144163 | A1 * | 7/2006 | Friberg | G01F 1/40 73/861.52 |
| 2007/0023034 | A1 | 2/2007 | Jongejan et al. | |
| 2007/0240712 | A1 | 10/2007 | Fleming et al. | |
| 2009/0294521 | A1 | 12/2009 | de la Huerga | |
| 2009/0308392 | A1 * | 12/2009 | Smutney | A61K 38/1709 128/203.15 |
| 2009/0314292 | A1 * | 12/2009 | Overfield | A61B 5/087 128/203.15 |
| 2010/0089394 | A1 * | 4/2010 | Sakurada | A61M 11/001 128/203.14 |
| 2013/0008436 | A1 * | 1/2013 | Von Hollen | A61M 15/009 128/200.14 |
| 2013/0221097 | A1 | 8/2013 | Day et al. | |
| 2013/0269694 | A1 | 10/2013 | Patton et al. | |
| 2015/0283337 | A1 * | 10/2015 | Adams | A63B 21/0088 128/203.15 |
| 2016/0001019 | A1 * | 1/2016 | Fink | A61M 11/005 128/200.14 |
| 2016/0144141 | A1 * | 5/2016 | Biswas | A61M 15/009 128/200.23 |
| 2016/0166766 | A1 | 6/2016 | Schuster et al. | |
| 2018/0369512 | A1 | 12/2018 | Blatchford et al. | |

FOREIGN PATENT DOCUMENTS

| | | | |
|---|---|---|---|
| EP | 2609954 | A2 | 7/2013 |
| JP | 2007-181724 | A | 7/2007 |
| JP | 2011-525138 | A | 9/2011 |
| JP | 2012-513828 | A | 6/2012 |
| WO | 2003035509 | A1 | 5/2003 |
| WO | 2005081977 | A2 | 9/2005 |
| WO | 2007001836 | A | 1/2007 |
| WO | 2007/101438 | A1 | 9/2007 |
| WO | 2009/155581 | A1 | 12/2009 |
| WO | 2010/078084 | A2 | 7/2010 |
| WO | 2011/056889 | A1 | 5/2011 |
| WO | 2012022771 | A2 | 2/2012 |
| WO | 2014/068504 | A2 | 5/2014 |
| WO | 2015003856 | A1 | 1/2015 |
| WO | 2015138454 | A1 | 9/2015 |
| WO | 2015/144442 | A1 | 10/2015 |
| WO | 2016009202 | A1 | 1/2016 |
| WO | 2016033418 | A1 | 3/2016 |
| WO | 2016033419 | A1 | 3/2016 |
| WO | 2016/111633 | A1 | 7/2016 |
| WO | 2016116591 | A1 | 7/2016 |
| WO | 2017005605 | A1 | 1/2017 |
| WO | 2017178865 | A1 | 10/2017 |
| WO | 2017201463 | A1 | 11/2017 |

OTHER PUBLICATIONS

United States Patent and Trademark Office Final Office Action mailed Apr. 27, 2023 for U.S. Appl. No. 16/854,669, filed Apr. 21, 2020.

Office Action issued in corresponding Japanese Application No. 2022-105253, dated Oct. 31, 2023, 3 pages.

Ngo, Kent et al., "Designing a digital inhaler", Master's Thesis, Feb. 2017, Lund University.

Howard et al., "Electronic Monitoring of Adherence to Inhaled Medication in Asthma", Current Respiratory Medicine Reviews, 10(1), pp. 50-63, 2014.

Notice of Opposition to related European Patent No. EP 3458133, dated Jul. 23, 2024, 25 pages.

* cited by examiner

FIG. 3
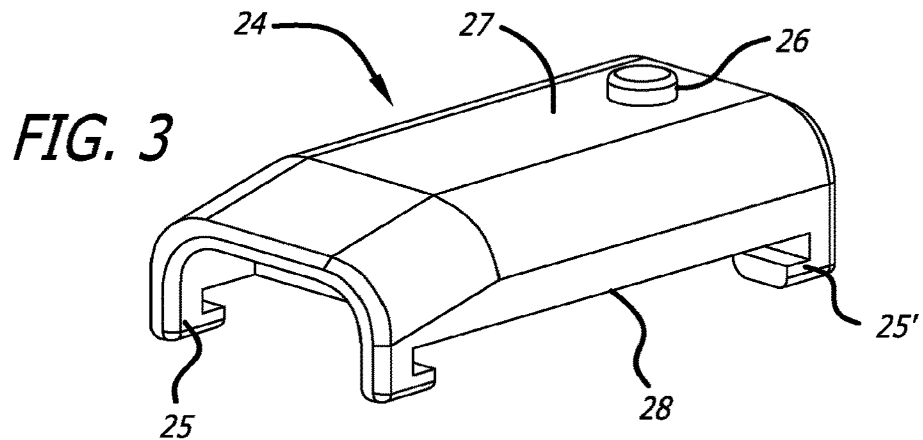
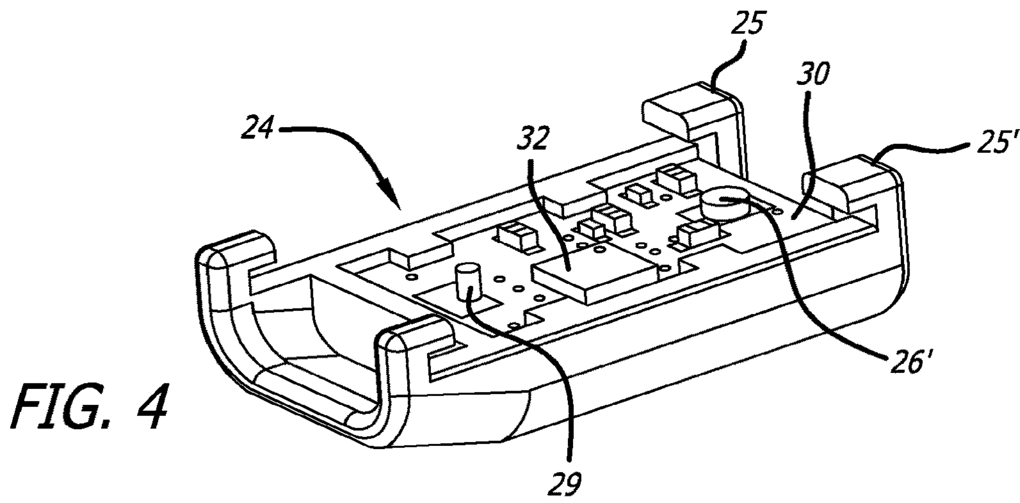
FIG. 4
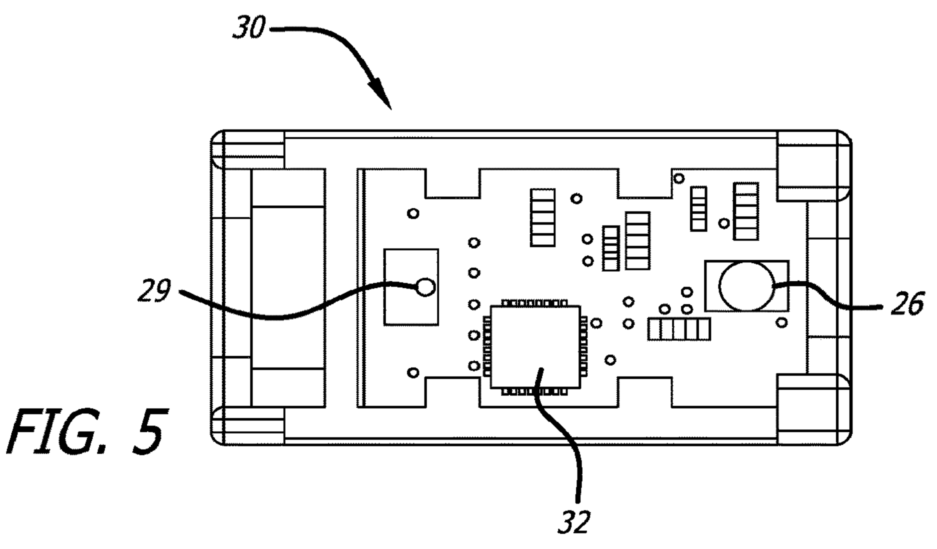
FIG. 5

82
USER
90
SENSOR 1
88
SENSOR 2
89
BATTERY
92
94
SIGNAL CONDITIONER
96
BANDWIDTH LIMITER
98
SIGNAL AMPLIFIER
95
A/D CONVERTER
97
OTHER DEVICES ON BOARD
99
MICROPROCESSOR
86
DISPLAY
84

100
USER
105
SENSOR 1
101
SENSOR 2
102
BATTERY
103
SIGNAL CONDITIONER
106
BANDWIDTH LIMITER
108
SIGNAL AMPLIFIER
109
A/D CONVERTER
112
OTHER DEVICES ON BOARD
115
MICROPROCESSOR
110
VISUAL INDICATORS
114

140
141
DIFFERENTIAL PRESSURE SENSOR
142
ABSOLUTE PRESSURE SENSOR
143
MICROPROCESSOR
144
DISPLAY
145
BATTERY
146
USER 150
151
DIFFERENTIAL PRESSURE SENSOR
152
ABSOLUTE PRESSURE SENSOR
153
MICROPROCESSOR
154
VISUAL INDICATORS
155
BATTERY
156
USER 180
181
DIFFERENTIAL PRESSURE SENSOR
182
ABSOLUTE PRESSURE SENSOR
183
MICROPROCESSOR
184
DISPLAY
185
BATTERY
186
USER
187
COLOR DETECTION SENSOR 190
191
DIFFERENTIAL PRESSURE SENSOR
192
ABSOLUTE PRESSURE SENSOR
193
MICROPROCESSOR
194
VISUAL INDICATORS
195
BATTERY
196
USER
197
COLOR DETECTION SENSOR

APPARATUS, SYSTEM AND METHOD FOR DETECTING AND MONITORING INHALATIONS

CROSS REFERENCE TO RELATED APPLICATIONS

This application is a continuation of U.S. patent application Ser. No. 16/301,700, filed Nov. 14, 2018, which is a 371 national stage application of PCT/US2017/033627, filed May 19, 2017, which claims the benefit of U.S. provisional patent application No. 62/338,971, filed May 19, 2016, the entire disclosures of which are incorporated herein by reference.

TECHNICAL FIELD

Described herein are interactive apparatuses and methods for recording, transferring and displaying physical measurements based on physiological conditions generated by a subject during an inhalation maneuver in real-time.

BACKGROUND

Inhaler devices for dispensing therapeutic substances via the respiratory tract, in particular, for pulmonary delivery in treating local or systemic diseases are commercially available. For example, nebulizers, devices containing propellants, and dry powder inhalers have been used for the treatment of diseases, such as asthma, respiratory tract infections and systemic diseases such as diabetes.

The efficiency of delivering the required dosage of a therapeutic substance to a patient in treating a disease depends on the efficiency of the device, and overall efficiency can be enhanced by providing proper feedback mechanisms to a patient, clinician or physician during use of the device to teach, for example, proper inhalation techniques to a patient. Improper use of the device and poor inhalation technique can lead to lack of efficacy in treating a disease. For example, administering lower or higher dosages of a therapeutic substance than intended can be harmful to a patient. To effectively deliver therapeutic substances to the respiratory tract, a patient or user can be trained or coached to use the device in an appropriate manner.

Dry powder inhalers used to deliver medicaments to the lungs contain a dose of a powder formulation usually either in bulk supply or quantified into individual doses stored in unit dose compartments, like hard gelatin capsules, cartridges, or blister packs. Dosing reproducibility requires that the drug formulation is uniform and that the dose can be delivered to the patient with consistent and reproducible results. Therefore, dosing can be improved by optimizing discharge of a formulation, which is effectuated, for example, by having patients perform proper inhalation maneuvers that achieve the necessary dosing.

Devices for training patients to properly deliver therapeutic substances by the pulmonary tract are described, for example, in U.S. Pat. No. 5,333,106, which discloses an apparatus for interactive training of a patient in use of an aerosol inhaler, including a feedback display based upon air flow versus volume data using a proper sequence of inhalation steps. U.S. patent application Ser. No. 10/759,859 (Publication No. US 2004/0187869) discloses a training device for medicament inhalers, for example, dry powder inhalers, which is based on measuring pressure differential and displaying a single value corresponding to both inhalation rapidity and inhalation flow rate peak, using a dry powder inhaler simulator.

Dry powder inhalers and cartridge systems, such as those described in U.S. Pat. Nos. 8,499,757 and 8,636,001, the disclosures of which are incorporated herein by reference in their entirety for all they teach regarding dry powder inhalers, can generate primary drug particles or suitable inhalation plumes during an inspiratory maneuver by deagglomerating a powder formulation within the inhaler and capsule or cartridge. The benefits of delivering drugs via pulmonary circulation are numerous and, include rapid entry into arterial circulation, avoidance of first pass drug degradation by liver metabolism and ease of use, for example, the lack of discomfort compared to other routes of administration such as by injection. These devices have been in use in clinical settings and are now commercially available.

An interactive apparatus and method for profiling of inhalation efforts is disclosed in U.S. Pat. No. 9,364,619, the disclosure of which is incorporated herein by reference in its entirety.

There is a need in the art for improvements in design and manufacture of inhaler devices which would maximize accuracy and require minimal training and effort for subjects in proper use of the inhalation system and monitoring patients during use of the inhalation system and their overall course of care and improvements to the flexibility of application to inhalers and inhaler parts including medicament packages and the reusability of such systems overall. The present disclosure presents apparatus and methods that achieve these goals.

SUMMARY

Described herein is an interactive apparatus for detecting and measuring inspiratory characteristic parameters of an inhalation system in use, including, inhalers and a patient's use of an inhaler in conjunction with the apparatus. In disclosed embodiments, the apparatus and method for using the apparatus are useful, for example, in sensing, detecting, measuring and monitoring a subject's characteristic inhalation profile, or breathing patterns, by collecting data generated from the subject's inhalation maneuver and identifying the effort required to deliver an appropriate or therapeutic dose with an inhaler provided to the subject for use in a treatment regimen. The apparatus and methods are also useful, for example, to train/teach a subject to use an inhaler for treating his/her disease, disorder or condition effectively so that the subject receives an appropriate dose of the medication being delivered. In an embodiment, the apparatus can comprise any inhaler, in particular, a high resistance, dry powder inhaler for delivery of one or more pharmaceutically active ingredients or medicaments to the lungs and thus the pulmonary and systemic circulation of a subject being treated. In some embodiments, the dry powder inhaler is breath-actuated and when in use by a patient, the patient can observe the magnitude of the effort exerted during an inhalation, which is displayed concurrently with the actual inhalation taking place.

Example embodiments of the inhalation apparatus and system disclosed herein comprise an inhaler accessory apparatus, which is a separate device; wherein the inhaler accessory apparatus is adaptable with or mountable onto an inhaler so that it can come in close contact to or mounted on an inhaler during use, and is removable from the inhaler after use.

In some embodiments, a detection and monitoring system is provided comprising an inhaler to be used by a patient and a corresponding inhaler accessory apparatus which is configured to adapt to the inhaler or adapt to one another so that the inhaler can be removed or disengaged from the inhaler accessory apparatus and the patient can take and use the inhaler for self-administration of a dose of a medicament, as prescribed by a physician for inhalation. The inhaler accessory apparatus comprises a body structurally configured to engage with the inhaler prescribed to the patient, an optional display means for displaying visual cues, including a display screen comprising, for example, light emitting diodes (LED) (e.g., for power ON and for battery charging status or other status), or liquid crystal display (LCD), touch screen or other interactive display, which can be miniaturized to adapt to the inhaler accessory apparatus or be located remotely in other parts of the detection and monitoring system and an electronic board comprising a microprocessor and one or more sensors. In some embodiments, the inhaler accessory apparatus comprises a receiver and transmitter or transceiver for sensing signals emanating from the inhaler which communicates wirelessly or wired to a computer, a personal data assistant (PDA), tablet, and/or a mobile phone to display information, in an application or otherwise, from an inhalation maneuver being performed by a patient or user in real-time, concurrently as it is taking place. The inhaler accessory apparatus preferably also includes a serial (e.g., USB) port or other port to permit data transfer and battery charging.

In some embodiments, a method is provided, which comprises providing an inhaler accessory apparatus for coupling to a subject's inhaler; activating the inhaler accessory apparatus system; having the subject inhale while monitoring the subject's inhalation with the inhaler accessory apparatus and facilitating training and/or monitoring the subject to achieve an optimal or appropriate inspiratory maneuver for the effective delivery of a therapy to the respiratory system. The detection and monitoring system facilitates the training of subjects for the proper use of an inhalation device in order to achieve a preferred flow profile for that individual so that optimal delivery of a medicament can be attained. The apparatus and method can also be used to monitor the performance of the inhalation system provided to a patient, for example, for detection of the dose being delivered; quantification of the drug being delivered, duration of discharge of a dose being delivered; number of doses administered to the subject, and to monitor the mechanical integrity of the inhalation system in real-time and/or storing the data for future analysis. In certain embodiments, the inhaler or parts of the inhaler (such as cartridges) to be used with the inhaler accessory apparatus can include codes or identifiers such as radio frequency identification (RFIDs), color codings, laser etchings, texts, and the like.

In an exemplary embodiment, the inhaler accessory apparatus for an inhalation monitoring system can be made to perform interactively, for example, the apparatus can comprise a wireless communication interface allowing for remote acquisition of data, which can be sent to a computer, tablet, smartphone or other microprocessor based-system providing an interactive display of data, storage of data and/or web-based transfer of information. Alternatively, other example embodiments can comprise a wired communication interface.

In one example embodiment, the apparatus can be adapted, for example, to a high resistance dry powder inhalation system, such as those described in U.S. Pat. Nos. 7,305,986 and 7,464,706, U.S. patent application Ser. Nos. 12/413,405 and 12/484,125 the disclosures all of which are incorporated herein by reference in their entirety for all they disclose regarding dry powder inhalers. The apparatus can comprise a dry powder inhaler with or without a cartridge containing a pharmaceutical formulation, one or more transducers including, electrical, electronic, electro-mechanical, electromagnetic, photonic or photovoltaic; such as pressure sensors, temperature sensors, sound sensors, and optical sensors; a signal conditioning circuitry and/or software program, a means for electronic signal communication and an output display. In such an example embodiment, the apparatus can be used with an analog or digital sensor, appropriate signal conditioners such as amplification, signal filtering, analog to digital conversion, a microprocessor for onboard processing, a wireless communicator in communication with a remote computer, tablet, mobile phone, or personal data assistant (PDA) for subsequent signal processing and/or real-time output display. The apparatus can be used to deliver pharmaceutical compositions contained in pre-metered unit dose cartridges containing an active ingredient for delivering to the pulmonary circulation. In alternative example embodiments, the sensing and monitoring device can be adapted onto or within an inhalation system comprising a dry powder inhaler with a cartridge that can be empty or can contain a dry powder suitable for pulmonary delivery.

Dry powders comprising microparticles suitable for pulmonary delivery are well known in the art including, for example, those disclosed in U.S. Pat. Nos. 8,499,757 and 8,636,001, the disclosures of which are incorporated herein by reference in their entirety for all they disclose regarding microparticles. In respective example embodiments, the dry powders, the active ingredient can be a protein, a peptide, or a polypeptide and combinations thereof, for example, and endocrine hormone such as insulin, glucagon-like peptide-1 (GLP-1), parathyroid hormone or analogs thereof.

In certain embodiments, a dry powder formulation for delivery to the pulmonary circulation comprises an active ingredient or agent, including a peptide, a protein, a hormone, analogs thereof or combinations thereof, wherein the active ingredient is insulin, calcitonin, growth hormone, treprostinil, palonosetron, tobramycin, filgastrin, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, pramlintide, oxyntomodulin, peptide YY, deoxyribonuclease 1, interleukin 2-inducible tyrosine kinase, Bruton's tyrosine kinase (BTK), inositol-requiring kinase 1 (IRE1), or analogs, active fragments, PC-DAC-modified derivatives, or O-glycosylated forms thereof, epinephrine, an antimicrobial or an antifungal. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin, parathyroid hormone releasing peptide (PTHrP), neurotransmitters agonists and antagonist, including, 5-hydroxytryptamine receptor, prostacyclin or $PGI_2$, epinephrine, norepinephrine, and analogs thereof.

In one example embodiment described herein the apparatus comprises a sensor in communication with the dry powder inhaler, wherein the sensor can detect at least one signal type, including pressure, flow, temperature, and sound signals generated from the dry powder inhalation system and can send a signal to at least one device for analysis, storage, printing or display. In such an example embodiment, the sensor is configured within the dry powder inhaler or adaptable to the dry powder inhaler and the sensor can be a microphone.

In an example embodiment, the inhalation system comprises a dry powder inhaler having high resistance to airflow and having a resistance value between about 0.065 (√kPa)/liter per minute and about 0.200 (√kPa)/liter per minute. High resistance inhalation systems can be provided with the sensing and monitoring apparatus. In some embodiments, the sensor can detect intrinsic characteristic signals generated by the inhalation system in use. In another exemplary embodiment, the sensor is a sound sensor which includes a sound detecting device or a microphone, configured to transmit the sound signal by wire or wireless communication mode to at least one another device in the system. The sensing and monitoring apparatus for dry powder inhalers described herein can further be associated with an analog to digital converter which communicates at least one signal such as a sound signal to a microprocessor configured to analyze and process the signal. In another example embodiment, at least one device is an analog to digital converter.

In one example embodiment, monitoring systems are described for a dry powder inhaler comprising: a monitoring device comprising at least one sensor; an analog to digital converter; a data storage medium, wherein the data storage medium includes a set of machine-readable instructions that are executable by a processing device to implement an algorithm, wherein the algorithm comprises instructions for manipulating the data including one or more of the steps of: receiving the data from at least one sensor; filtering the data; transforming the data; analyzing the data; and monitoring a patient using the data.

In an example embodiment wherein at least one sensor is a microphone, the sensor is provided any place within the inhaler, for example, within the airflow conduits, within the wall of the inhaler, or outside of the inhaler as a separate piece. In another example embodiment, the monitoring device can be a detachable device that can be mountable on, or attachable to a dry powder inhaler. In yet another example embodiment, the monitoring device provides a graphical display which is a real-time graphical representation of an inhalation.

In another example embodiment, the sound signal is an amplitude of sound signal, a frequency of sound signal or combinations thereof. In yet other example embodiments, the sensor further measures at least one sound signal at different frequencies. In another example embodiment, the dry powder inhalers further comprise a cartridge and the cartridge can comprise a dry powder for pulmonary delivery. Further still, the dry powder can comprise diketopiperazine microparticles and at least one active ingredient. In still another embodiment, at least one medicament comprises insulin, GLP-1, parathyroid hormone, calcitonin, analogues thereof, or combinations thereof.

In a further embodiment, the sensing and/or monitoring device is configured to detect signals from a dose being delivered. In this embodiment, the sensing and monitoring system can detect movement of powder particles within the inhaler and a cartridge system in use from initiation of powder delivery from the cartridge to the end of delivery of the powder particles, wherein the sensor detects variations in the intrinsic characteristics of inhaler sound and powder particle sound emanating from the inhalation system. Data obtained from the detection can be analyzed and correlated to the amount of dose emitted or delivered out of the inhalation system, the time that elapsed for dose delivery, and the performance of the inhalation system.

In another example embodiment, the sensing and monitoring apparatus can be provided as an adaptable, detachable device such as a jacket or saddle structure to a dry powder inhaler. In this embodiment, the removable device facilitates use of the inhalation system, since the structure or configuration of the dry powder inhaler is not modified. Therefore, the same inhaler can be used without the jacket once the characteristic performance of the inhaler has been determined and the subject can properly use it. In embodiments herein, the sensor such as a small microphone, can be advantageously placed in any area of the jacket, including, for example, embedded in the wall of the jacket or adaptor, or extending from the walls of the jacket. In this embodiment, the sensing and monitoring apparatus offers greater resolution of sound characteristics emanating from the dry powder inhaler and cartridge system in use.

In one embodiment, methods are described for measuring pressure differential during an inhalation maneuver, the methods comprise: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, said at least one frequency of sound signal, or combinations thereof using an algorithm provided with a microprocessor in a computer system to generate a data set; and displaying, printing, or storing the data set as a function of time and pressure.

In further embodiments described herein are monitoring systems for a dry powder inhalers comprising: a monitoring device comprising at least one sensor; including an acoustic sensor, a Doppler; an analog to digital converter; a data storage medium, the data storage medium including a set of machine-readable instructions that are executable by a processing device to implement an algorithm, the algorithm comprising instructions for manipulating the data including the steps of: receiving the data from the at least one sensor; filtering the data; transforming the data; analyzing the data; and monitoring a patient using the data.

Even further still, in some embodiments described herein are methods for measuring pressure differential during an inhalation maneuver, comprising: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, the at least one frequency of sound signal, or combinations thereof using an algorithm provided with a computer system to generate a data set; and displaying, printing, or storing the data set as a function of time and pressure.

In other embodiments described herein are interactive dry powder inhalation systems for monitoring an inhalation performed by a user, comprising: an inhaler accessory apparatus comprising at least one microprocessor, one or more active sensors including, a Doppler effect sensor and/or an infrared sensor which can measure a flow of air or a gas; a dry powder inhaler comprising a cartridge having type identifiers, such as color, laser etchings, printed numbers; printed words to be recognizable by a sensory beam including a laser beam, RFID, optical recognition, image sensors and the like, the sensory beam can detect identifier codes integrally configured with the cartridge for detecting colors, type of dose; amount of dose, etc. Image detection sensors may be used in conjunction with on board or remote computing to detect dose or other identifiers using optical character recognition. In some embodiments, the dry powder inhaler has a resistance to flow values between 0.065 (√kPa)/liter per minute and 0.200 (√kPa)/liter per minute; a transducer configured to detect a signal generated from the inhaler in use, and a display device configured to display in real-time an inhalation maneuver performed by a user. In another embodiment, the transducer senses and measures a pressure differential within the inhaler. Further still, the transducer can be a flow meter configured to sense and measure flow rate through air conduits of the dry powder inhaler. The transducer can be, for example, a microphone configured to sense and measure a sound signal generated from within the inhaler.

In still other embodiments described herein are sensing and monitoring devices for adapting to a dry powder inhaler, comprising: a detachable device structurally configured to adapt to a dry powder inhaler; said detachable device comprising a microphone for detecting sound generated in said dry powder inhaler; and wherein the dry powder inhaler has a resistance to flow value between 0.065 (√kPa)/liter per minute and 0.200 (√kPa)/liter per minute.

Further, in some embodiments, sensing and monitoring devices are described for a dry powder inhalation system, wherein the dry powder inhalation system comprises a dry powder inhaler and a cartridge and the sensing and monitoring device comprises a microphone configured to detect sound signals generated from a dry powder formulation emitted from the dry powder inhalation system.

In some embodiments, the dry powder inhaler comprises a housing, a moveable member, and a mouthpiece, wherein the moveable member is operably configured to move a container from a powder containment position to a dosing position. In this and other embodiments, the moveable member can be configured as part of a lid assembly at the proximal end of the inhaler and forms a portion of the cartridge mounting are. In this embodiment, the mouthpiece is integrally built with a lid or cover portion which covers the housing over the cartridge mounting area upon closing the inhaler. Movement of the mouthpiece in a downwardly direction from the horizontal plane, moves the lid or cover in an angular direction to a vertical position and opens the inhaler to give access to the interior of the inhaler to allow for loading and unloading a cartridge. Conversely, movement of the mouthpiece in an upward direction from a vertical plane to a horizontal plane induces closure of the inhaler and automatically generating an opening of an air pathway between the inhaler and a cartridge loaded onto the cartridge mounting area.

In another embodiment, the dry powder inhaler comprises a body, a housing and a mouthpiece; the inhaler is structurally configured to have an open position, a closed position and a mechanism operably configured to receive, hold, and reconfigure a cartridge from a containment position to a dispensing, dosing or dose delivery position upon movement of said inhaler from the open position to the closed position. In versions of this embodiment, the mechanism can also reconfigure a cartridge installed in the inhaler from the dosing position to a containment position after use when the inhaler is opened to unload a used cartridge. In some embodiments, the mechanism can reconfigure a cartridge to a disposable or discarding configuration after use.

In some embodiments, the body of the inhaler comprises a proximal portion comprising the mouthpiece, a body and a distal portion comprising a housing which is structurally configured as a slip-on cover over portions of the body and internal parts of the inhaler; wherein the housing comprises a distal end and a proximal end and the proximal end has an opening for adapting and encapsulating portion of the inhaler body. In some embodiments, the proximal end contacts or abuts the inhaler body so as to close the inhaler from the external environment. From the closed configuration the inhaler is opened by movement of the housing in a distal direction over the body in a translational motion to attain an inhaler loading and/or unloading position to insert or remove a cartridge. With a cartridge installed in the inhaler, translational movement of the housing over the body in a distal to proximal direction causes cartridge displacement from a containment configuration to a dosing configuration, wherein the cartridge container is pushed to the dosing configuration by a projection configured in the interior of the housing that extends beyond the opening at the proximal end. In the closed configuration, a cartridge installed in the inhaler is reconfigured to form an additional air passageway with the mouthpiece and ambient air to access a dry powder in cartridge in the dosing configuration upon inhalation. In this and other embodiments, the air passageway of a cartridge in a dosing configuration has an air inlet, an air outlet in communication with an air passageway in the mouthpiece, wherein the mouthpiece has its own air inlet and an air outlet.

In some embodiments, the body of the inhaler comprises a mouthpiece formed at a proximal end of the body and has an air conduit which is in communication with the interior of the housing and can be in direct communication with an air outlet of a cartridge installed in the inhaler and with ambient air. The inhaler body also comprises a cartridge mounting area which is continuous in structure with the mouthpiece and has a distal part and a proximal part; wherein the proximal part and the distal part form one single piece with the mouthpiece and is insertable in the housing. In some embodiments, the body and the housing can be pulled apart to attain an inhaler open configuration for access to an internal compartment. In an open configuration of this embodiment, a cartridge comprising a dry powder can be loaded or install in a cartridge mounting area of the body, and the body and housing can be pushed or pulled to either open or close the inhaler. In some embodiments, the housing is moveable over the distal part of the body from an open to a closed configuration, and together they close the inhaler and effectuate the forming of an air conduit through a cartridge mounted in the cartridge mounting area. In this configuration, the inhaler attains a dosing configuration for a powder in the cartridge to be emitted from the inhaler upon an oral inhalation by a user through the mouthpiece. In this embodiment and the dosing configuration, the body and the housing abut one another and are adapted tightly together by one or more anti-slip structures to prevent the inhaler from coming apart. Examples of anti-slip features are snap rings, or detents, which can generate a sound to alert a user that the inhaler is ready for use. In some embodiments, the inhaler is substantially rectangular in shape with the distal and proximal sides being smaller in length; wherein movement of the housing over the body, or vice versa, is effectuated by pulling or pushing and the inhaler body having guide rails or tracks extending outwardly from the longer sides (a first side and a second side) of the inhaler in a longitudinal plane. In this embodiment, the inhaler body is designed to have an opening at its distal end to match the opening at the distal end of the housing to allow and guide ambient air into the interior chamber of the inhaler upon inhalation. The housing is also fittingly configured to have grooves or slots for gliding over the guide rails during movement and also comprises stop ends to prevent disassembly of the inhaler, and a pushing element for positioning a cartridge in a dosing configuration after installation and closing of the inhaler. The pushing element moves the cartridge cup or container relative to the cartridge lid to form an air passageway through the cartridge and create an air inlet and an air outlet and allow aerosolization of a powder in the cup during an inhalation for delivering the aerosolized particles to the inhaler mouthpiece and into the user. In another embodiment, the pushing element also moves the cartridge assembly to position the lid relative to the inlet opening located in the floor of the mouthpiece. In one aspect of this embodiment, the dry powder inhaler comprises a housing comprising a pushing element, wherein the housing positions the cartridge to align with the mouthpiece by translation of the housing over the inhaler body from an open configuration to a closed configuration.

In some embodiments, the dry powder inhaler comprises a housing having a distal end and configured with an opening for communicating with ambient air. In some embodiments, the housing is configured in the shape of a cover which slips over the inhaler body, to substantially envelop a portion of the body of the inhaler, the housing moves translationally over the distal part of the body; wherein the inhaler can attain two configurations, a first position which opens the inhaler to access its interior compartment, a chamber; and a second position which abuts the proximal end to attain closure of the inhaler. In some embodiments, the distal portion of the housing is also moveable with respect to the proximal end in a horizontal plane to extend distally and allow for access to the internal compartment of the inhaler and over, surrounding the inhaler body. In versions of this embodiment, the distal portion of the housing comprises parallel structures or flanges for engaging portions of the body of the inhaler and form a securing mechanism, for example, for locking the body of the inhaler with the housing to secure the two parts together and maintain the dosing configuration. In an embodiment, the distal portion of the housing has an opening at its distal end for communicating with the interior of the inhaler and an opening which is configured to slide over the inhaler body. The distal portion of the housing also comprises an external surface, an interior surface and a chamber configured to slide over the inhaler body. In some embodiments, the distal portion of the inhaler comprises parallel wing-like structure on its upper surface for directing airflow into the mouthpiece during an inhalation.

In an alternate embodiment, the mouthpiece is engaged to the body of the inhaler by various mechanisms including, a moveable member such as a hinge and is integrally configured with a moveable assembly, including a rack for moving a cartridge lid relative to cartridge cup or container. The moveable assembly is configured to receive and reconfigure a cartridge installed in the inhaler from a containment position to the dosing position can be designed to operate manually or automatically upon movement of the inhaler components, for example, by closing the device from an open configuration. In some embodiments, the mechanism for reconfiguring a cartridge comprises a slide tray or sled attached to the mouthpiece and movably attached to the housing. In another embodiment, the mechanism is mounted or adapted to the inhaler and comprises a geared mechanism integrally mounted within, for example, a hinge of the inhaler device. In yet another embodiment, the mechanism operably configured to receive and reconfigure the cartridge from a containment position to a dosing position comprises a cam that can reconfigure the cartridge upon rotation of, for example, the housing or the mouthpiece. In some embodiments, angular rotation of the mouthpiece from the horizontal plane opens the inhaler to allow installation or removal of a cartridge and angular movement or the mouthpiece from a vertical plane to the horizontal plane effectuates closure of the mouthpiece and automatic reconfiguration of a cartridge from containment to dosing position. In an embodiment, the gear mechanism during actuation positions the cartridge lid relative to the inlet opening in mouthpiece and effectuates translation of the cup to a dosing configuration.

In some embodiments, the inhaler to be used by a subject is provided to the subject and the patient inhalation profile is determined using an inhaler accessory apparatus adapted to the inhaler by activating the inhalation apparatus and system and asking the patient to take a breath using the inhaler mouthpiece. Concurrently with the patient's breath, the inhaler accessory apparatus implements the display of the data detected and monitored by the system or indicators relating to such data which is generated from the patient's breathing in real-time. In this and other embodiments, the display can be viewed on a mobile phone, tablet, PDA or computer comprising an algorithm application, which communicates with a microprocessor on the inhaler accessory apparatus comprising a microwave radio signal transmitter and receiver, or a transceiver, such as Bluetooth®, Zigbee®; WiFi, SmartWave, or Z-Wave, the microwave radio signals capable of being detected by an application provided in a mobile phone which can communicate with the inhaler accessory device. In an embodiment, the microwave radio signals from the transceiver can be transmitted from the microprocessor and can be received by a transceiver in a computer for communicating with each other. In an embodiment wherein the inhaler accessory apparatus communicates with a tablet, personal digital assistant (PDA) or mobile phone, wherein the tablet, PDA or mobile phone can access a programmed application which displays a screen with a graphical interface which when turned on can communicate with the inhaler accessory apparatus and detect any information/signal generated from the inhalation system.

BRIEF DESCRIPTION OF THE DRAWINGS

FIG. 3 illustrates a top isometric view of an embodiment of a wireless detecting and sensing inhaler accessory apparatus.

FIG. 4 illustrates a bottom isometric view of an embodiment of a wireless detecting and sensing inhaler accessory apparatus, showing an electronic board.

FIG. 5 illustrates a top view of the electronic board of FIG. 4.

DETAILED DESCRIPTION

Figure 1:
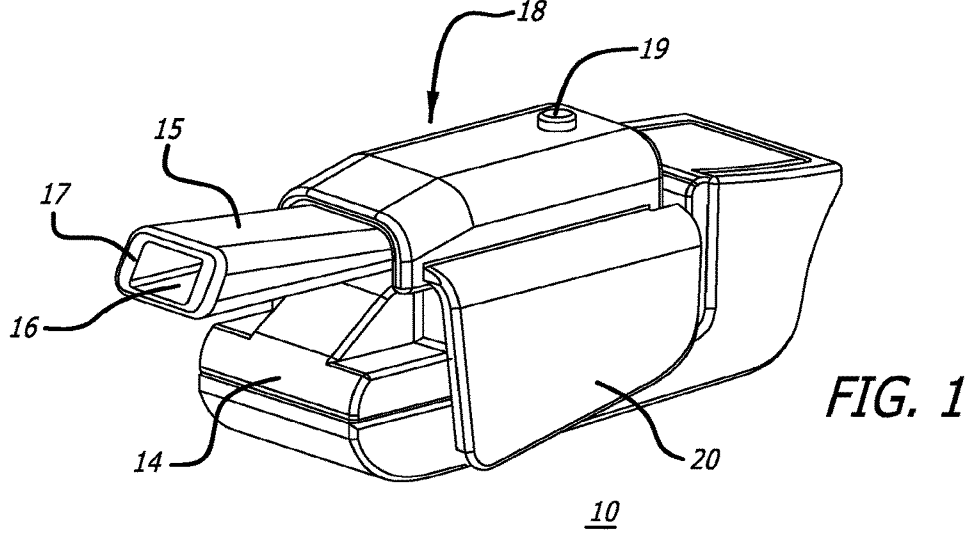
FIG. 1 illustrates an isometric view of an embodiment of a wireless dry powder detecting and sensing inhaler accessory apparatus mounted on an inhaler.

Disclosed herein are apparatus and/or devices with interactive system and methods for measuring or monitoring real-time characteristic changes in pressure or pressure drop and/or flow from a subject during an inhalation maneuver with an inhaler. The devices can be used for detecting and monitoring and consequently training a subject to maximize efficiency of their respiratory maneuvers in conjunction with an inhalation device, and can also be used for monitoring inspiration during delivery of a medicament, to detect proper dose delivery, timing of dose delivery and proper performance of the inhalation system in use. In one example embodiment, the sensing and monitoring apparatus can be applied in conjunction with a high resistance inhaler. In embodiments herein, the detection and monitoring system can measure many characteristic parameters of an inhalation maneuver using inhalers, in particular, in conjunction with dry powder inhalers, which include data generated for assessing peak inhalation effort within two seconds of onset of an inhalation ($PIP_2$), total inhalation effort in the first second of an inhalation ($AUC_1$), total inhaled volume and the duration of an inhalation of patient inhalation efforts. Although the handheld inhaler system is described as comprising two parts—an inhaler and an inhaler accessory apparatus, one skilled in the art can appreciate that the inventive design of this system and method for measuring or monitoring data and characteristics during an inhalation maneuver can also apply to a device where the accessory features are integrated into the inhaler itself, albeit sacrificing flexibility and reusability.

The apparatus comprises an inhaler accessory apparatus adapted for mounting on or otherwise associating with an inhaler. The apparatus comprises at least one transducer or sensor which can detect at least one measurement, including pressure, air flow, air volume, humidity, and temperature, and convert such into an electrical signal. In some embodiments, the sensor can comprise a Doppler sensing device which can detect a flow of air or a gas through an inhaler. In other embodiments, the sensor comprises a pressure sensor which can detect pressure drop during an inhalation maneuver. The inhaler accessory apparatus can further include an electronic board with circuit elements including appropriate signal conditioning circuitry, such as signal filtering, amplification and analog to digital conversion, and processing circuitry such as a microprocessor, wired or wireless communication interface and the like to transfer the generated signal concurrently or in real-time to a receiving computer or personal data assistant (PDA), including a mobile telephone for display of the signal or processed information. In some embodiments, the output display can be an interactive display so that the display device provides a visual aid for allowing a physician and/or patient to view the inhalation maneuver parameters attained. In this manner, the information obtained can serve as a teaching guide for a subject to perform repeatable inhalation maneuvers in real-time, thereby facilitating proper inhalation delivery of a medicament when is self-administered. In another example embodiment, the data can be stored to be analyzed at a later date.

FIGS. 1 through 7 illustrate embodiments of a dry powder inhaler system or training device and its component parts. The training devices interactive systems described herein have been adapted to a high resistance dry powder inhaler as disclosed in U.S. Pat. Nos. 8,499,757, 8,636,001 and U.S. Provisional Patent Application Ser. No. 62/289,095, the disclosures of which are incorporated by reference herein for all they disclose regarding dry powder inhalers.

Figure 2:
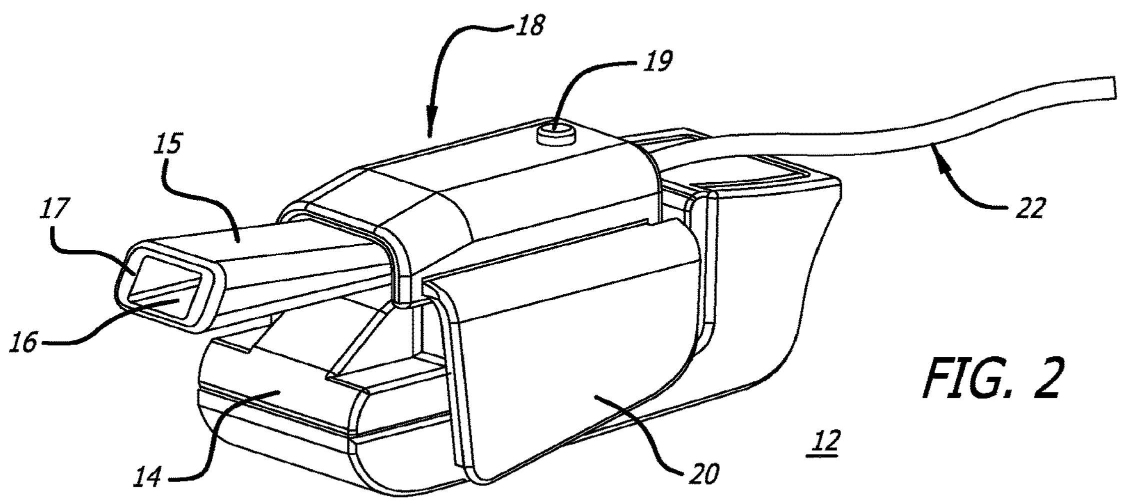
FIG. 2 illustrates an isometric view of an embodiment of a wired dry powder detecting and sensing inhaler accessory apparatus embodiment mounted on an inhaler.

FIG. 1 and FIG. 2 depict, respectively, a wireless and wired inhalation detection and monitoring system 10, 12. The system comprises an inhaler 14 comprising a mouthpiece 15 having an air conduit 16 and an air outlet port 17 for delivering a powder to a user/patient. The inhalation detection and monitoring system 10, 12 also comprises an inhaler accessory apparatus 18 adapted for mounting on, connecting with or otherwise associating with the inhaler 14. In this embodiment, the inhaler accessory apparatus includes an actuator button 19 for powering ON/OFF the system 10, 12. An air conduit is established between one or more air inlet ports for establishing air conduit pathways through the system which at least one air conduit pathway travels through a receptacle containing a dry powder for delivery to an individual in use. In some embodiments, the inhaler does not contain any powder during training of a patient for proper use of the inhaler. In the embodiment of FIGS. 1 and 2, inhaler 14 is of the same type, which is a dry powder inhaler, and the inhaler accessory apparatus 18 is adaptable to the top surface of inhaler 14. FIG. 2 depicts inhaler accessory apparatus 18 having a wire 22 connected to the system for connecting to a power source and/or to a computer.

FIG. 3 illustrates a top isometric view of another embodiment of an inhaler accessory apparatus 24 designed for adapting to an inhaler. FIG. 4 illustrates a bottom isometric view of the apparatus 24. As can be seen in FIGS. 3 and 4, accessory apparatus 24 preferably comprises a body having tabs 25, 25' to attach to an inhaler. However, other types of securing devices known to those skilled in the art can be used to engage apparatus with inhaler. The apparatus 24 also preferably includes an actuator button 26 for activating the apparatus for use. In this embodiment, the body has a top surface 27, a bottom surface 28 and an electronic board 30 mounted to the bottom surface. FIG. 4 illustrates an embodiment of an inhaler accessory apparatus 24 having an electronic board 30 integrally built into its undersurface 28. FIG. 4 and FIG. 5 further illustrate electronic board 30. Electronic board 30 preferably comprises actuator 26' which is mechanically or otherwise connected to actuator button 26, sensor 29, and microprocessor 32. Microprocessor 32 provides for actuating, detecting, processing signals from an associated inhaler and communicating the information/signals to a display device. In this embodiment, electronic board 30 is configured as a signal processing/interface board. Sensor 29 can be any type of sensor such as an acoustic sensor for detecting sound generated during an inhalation or a pressure sensor for detecting pressure drops during an inhalation. The inhaler accessory apparatus 24 is also preferably provided with a battery as a power source for activating the system when the actuator button is depressed. One skilled in the art will appreciate that the electronics included in inhaler accessory apparatus 24 can be provided as separate circuit components on separate boards connected by appropriate means as necessary for functionality. For instance, the microprocessor 32 can reside on a separate board from sensor 29 due to necessity of placement of the sensor 29.

Figure 6:
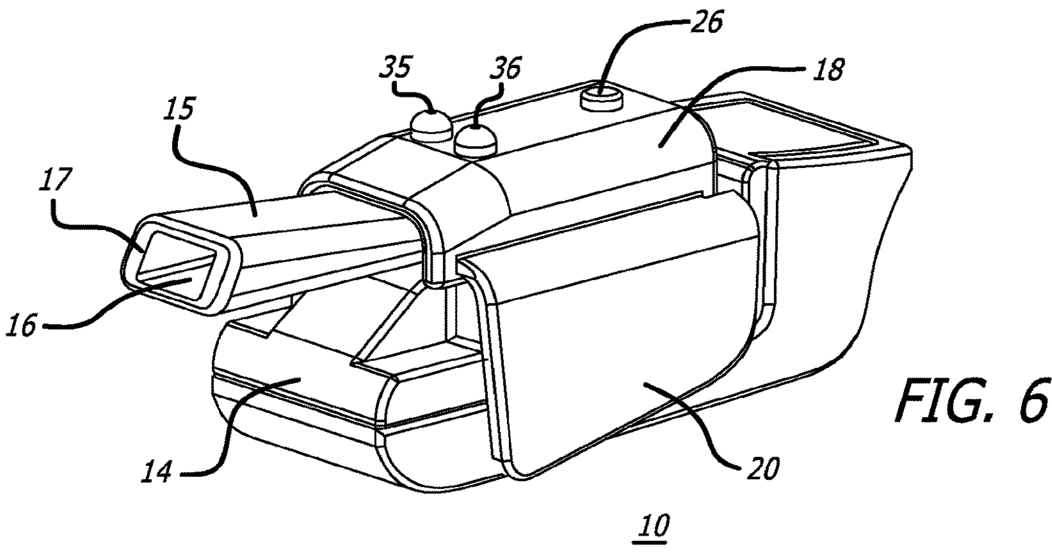
FIG. 6 illustrates an isometric view of a dry powder inhaler coupled to an embodiment of a detecting and sensing inhaler accessory apparatus as shown in FIG. 1 including integrated signal indicating buttons.
Figure 7:
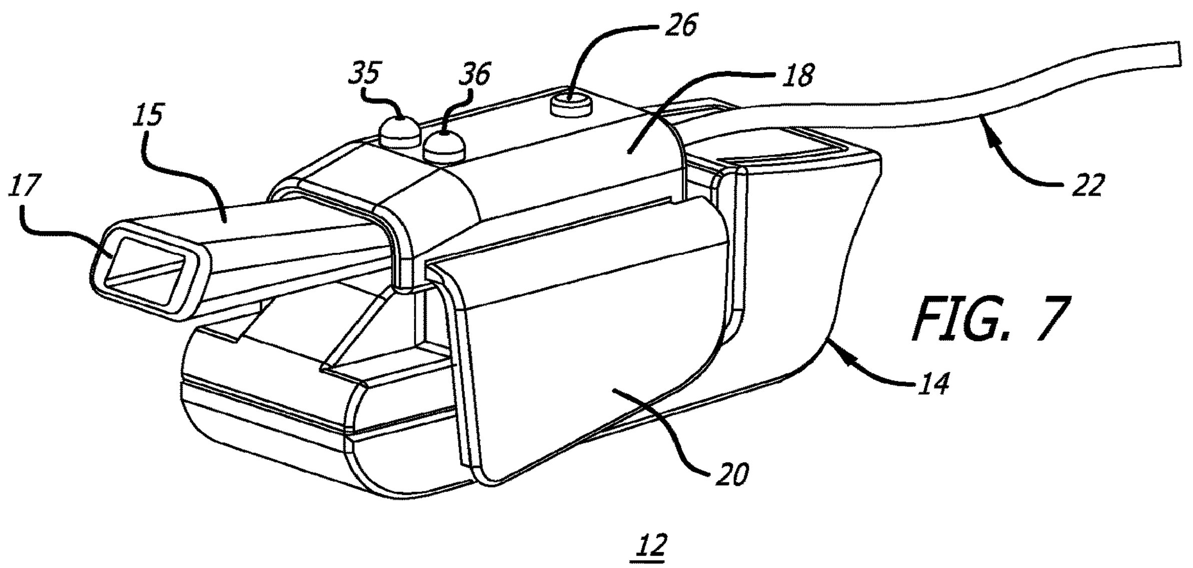
FIG. 7 illustrates an isometric view of a dry powder inhaler coupled to an embodiment of a detecting and sensing inhaler accessory apparatus as shown in FIG. 2 including local signal indicating buttons.

In another embodiment, the inhalation detection and monitoring system is provided with indicators as shown in FIGS. 6 and 7. FIG. 6 illustrates an isometric view of a dry powder inhaler coupled to an inhaler accessory apparatus as shown in FIG. 1 showing signal indicators 35, 36. FIG. 7 illustrates an isometric view of a dry powder inhaler coupled to an inhaler accessory apparatus 18 as shown in FIG. 2 showing signal indicators 35, 36. Signal indicators 35, 36 are preferably light emitting diodes or other light indicators for indicating certain status to the user. For example, they can be used to indicate whether an inhalation resulted in successful inhalation of the medicament. In this case, for example, one indicator can show a red signal light and another can show a green signal light during operation. The signal indicators 35, 36 would correspondingly indicate fail or pass. A fail inhalation indicator (red light) indicates that the subject or patient's inhalation maneuver executed did not meet one or more predetermined criteria for inhaling a powder dose contained in the inhaler, and a pass inhalation indicator (green light) indicates that the subject or patient's inhalation maneuver meets the appropriate criteria for delivering a powder dose contained in the inhaler. Alternatively, only one signal indicator can be used if color can be selected based upon status or, for instance, if flashing can be used to indicate status. Other uses of signal indicators 35, 36 could include power ON/OFF, power failure or battery low indication or status of connection between accessory apparatus and inhaler.

Figure 8:
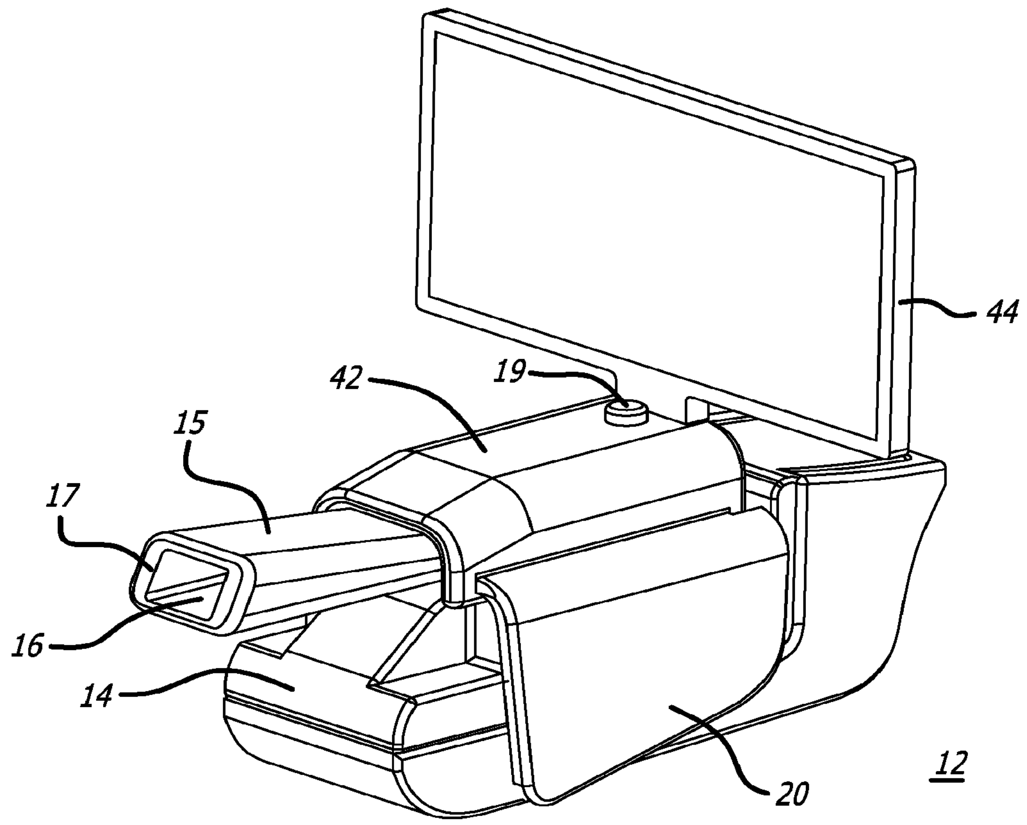
FIG. 8 illustrates an isometric view of an embodiment of a wireless dry powder detecting and sensing inhaler accessory apparatus mounted on an inhaler and including an integrated display screen.

FIG. 8 depicts an isometric view of an alternate embodiment of a wireless dry powder detecting and sensing inhalation system 12 wherein the inhaler accessory apparatus 42 is shown mounted on an inhaler 14 and configured with a display screen 44 integrally configured on the body of the accessory apparatus 42 so that the patient can visualize the inhalation maneuver concurrently with his/her inhalation effort. In this embodiment, the inhaler accessory apparatus 42 comprises an electronic board 30 as shown in FIGS. 4 and 5 wherein the signal information relating to the inhaler is processed in the microprocessor 32 and the resultant processed information is communicated to the display screen 44 and presented preferably as a graphical display compared to one or more predetermined criteria for the inhaler used. This graph and associated data points are preferably stored locally on electronic board 30 but can also be stored remotely. In this and other embodiments, the predetermined criteria for an inhaler depends on the inhaler and medicament being used. In some embodiments and shown in the figures herewith, the criteria used is as indicated above as peak inspiratory pressure, emitted dose and the like.

Figure 9:
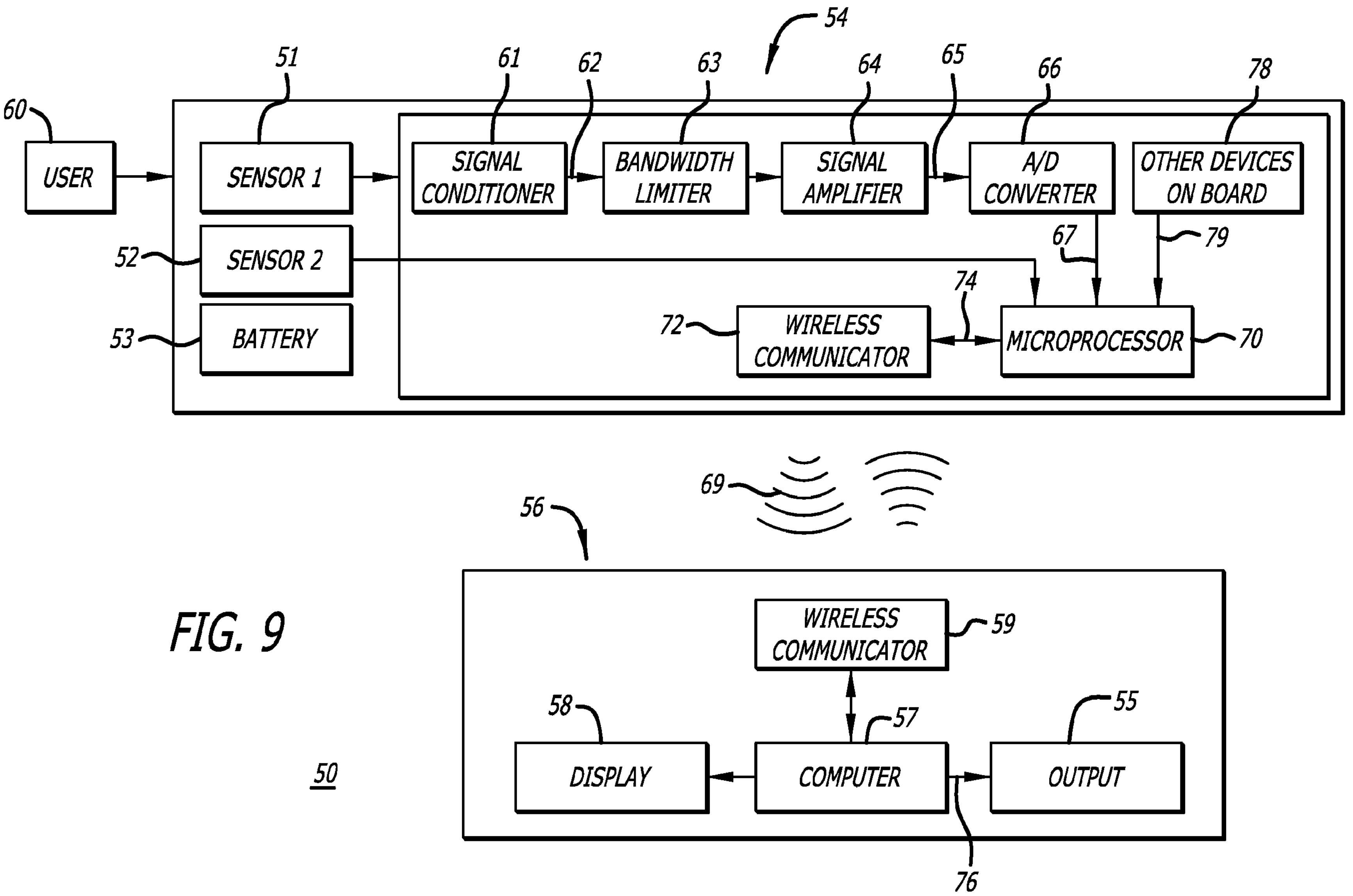
FIG. 9 illustrates a block diagram of an overall embodiment of a wireless detection and monitoring system disclosed herein.
Figures 10, 11:
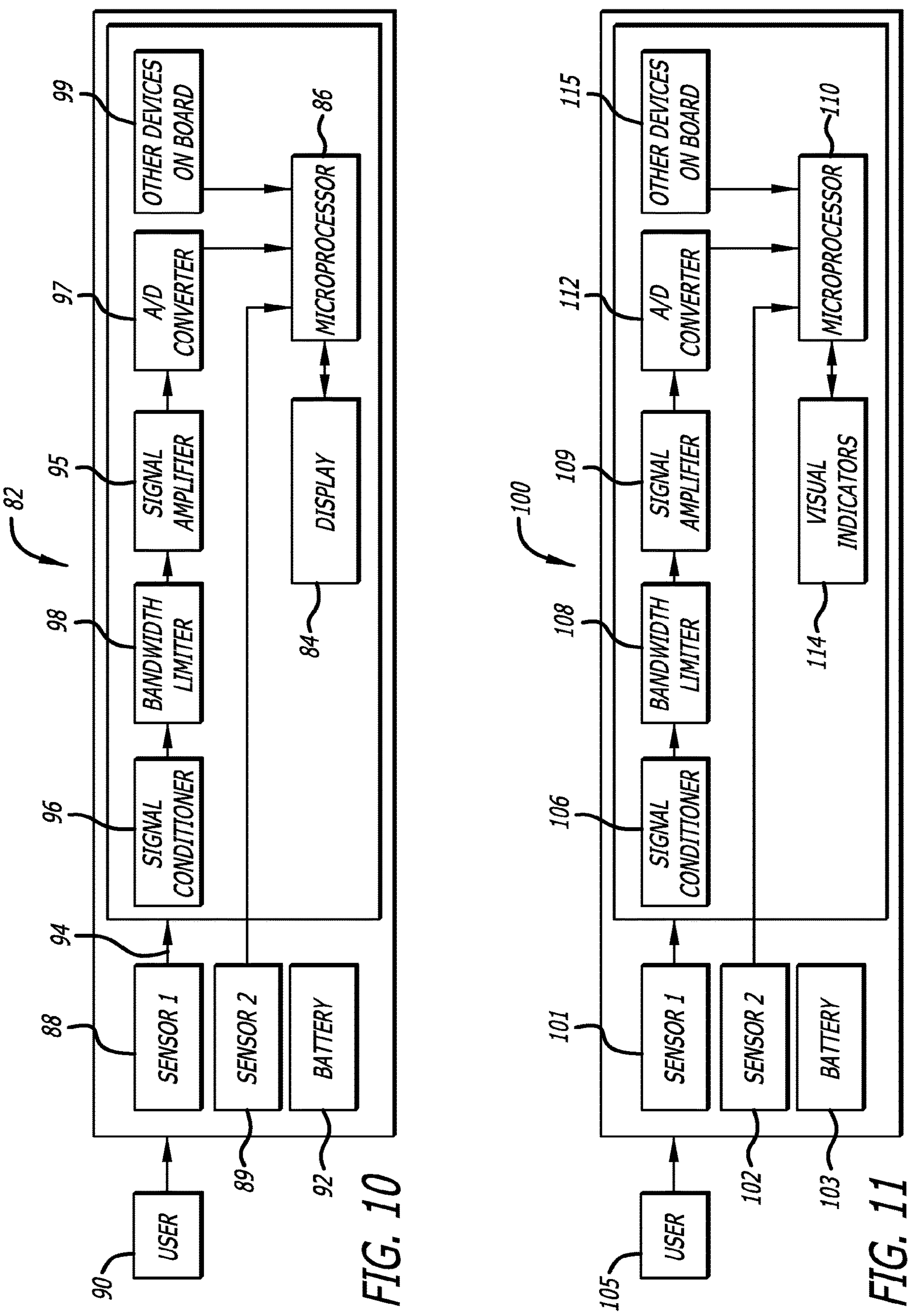
FIG. 10 illustrates a block diagram of an embodiment of a detection and monitoring system disclosed herein.
FIG. 11 illustrates a block diagram of another embodiment of a detection and monitoring system disclosed herein.

FIGS. 9, 10 and 11 illustrate various operational embodiments of the inhalation detection and monitoring system shown in FIGS. 1-8. FIG. 9 illustrates a block diagram of an overall embodiment of a wireless detection and monitoring system 50 disclosed herein. In FIG. 9, system 50 comprises two components, accessory apparatus 54 and processing system 56. In this embodiment, the inhaler accessory apparatus 54 comprises an electronic board having two sensors 51, 52, battery 53 a microprocessor 70 and a wireless communicator or transceiver 72. Analog sensor 51 and digital sensor 52, are placed so that they are in close proximity to the inhaler airflow conduits so as to be able to detect a sound signal or a pressure differential in the inhaler 14 when inhalation detection and monitoring systems 10, 12 are actuated or turned on. The system is powered on by depressing actuator button 19, 26 which is connected to a power source, such as battery 53 that also provides power to the system. Alternatively, the system can be powered by a wire such as a USB port. Sensors 51, 52 are preferably placed at any point within or proximate to the air conduit of inhaler accessory device 18, 24. In some example embodiments, sensor 18, 24 can be placed in the air conduit within body 20 of the accessory device or near the mouthpiece 15 of the inhaler being used.

Processing system 56 can include a PDA, tablet, mobile telephone, or computer 57, display 58, wireless communicator 59 and output 55 which can be in the form of digital storage, a web interface, a print out or an email or the like. It should be appreciated by one skilled in the art that the display 58, wireless communicator 59 and output 55 could simply reside within the PDA/tablet/mobile phone/computer 57 rather than being separate elements. In this example embodiment, a user can activate inhaler accessory apparatus 54 by depressing a power button, for example button 19 on apparatus 10, with processing system 56 also activated. Computer 57 preferably includes an algorithm in the form of a software application or program designed to collect and display inhalation effort. When the software program integrated with computer 57 is initiated, a start signal appears on display 58. With the system activated, a user's inhalation 60 generates a pressure drop in inhaler training device 50, which is transduced to an electrical signal by one or more of sensors 51, 52. In this embodiment, the sensors 51, 52 can be a pressure, flow, sound, optical, gas, humidity, or temperature transducer that is either analog or digital. Electrical signal generated from sensor 51 is then transmitted to signal conditioner 61 to remove unwanted portions of signals, such as signal noise. Conditioned electrical signal 62 is then transmitted to bandwidth limiter 63 to reduce the frequency of the signal to a desired range to reduce and select the data needing to be analyzed and the signal is then transmitted to a signal amplifier 64 and in signal amplifier 64, the selected signal can be amplified to a predetermined voltage range, and transmitted as amplified signal 65. Amplified signal 65 is then converted to digital signal 67 through analog to digital converter 66. It should be appreciated by one skilled in the art that certain "smart" sensors can be used which integrate certain of the conditioning, filtering, amplifying and converting functionality into the sensor itself. Therefore, any reference to these subsequent elements in this specification can be replaced by use of such integrated sensors. Digital signal 67 is then received by microprocessor 70 and is transmitted into wireless communicator or transceiver 72 designed for transmission using a wireless technology standard such as Bluetooth® through connection 74 for transmission to computer 57, having wireless communicator 59 for receiving wireless (e.g., Bluetooth®) signal 69. A software program built/programmed into microprocessor 70 or computer 57 facilitates basic functionality in the inhaler accessory apparatus including advertising wireless presence, linking to wireless communicator or transceiver 59 and passing data from element to element and over wireless signal 69. The program also converts electrical signals from sensor 1, 2 to a pressure value which can be displayed graphically in display 58. Display 58 can be a screen comprising LED, OLED, LCD, touch screen, or other interactive display. In certain embodiments, a baseline curve for the user is stored in the system 50 and provided on the display 58 along with the inhalation signal information. The baseline curve is indicative of the level of performance for an inhaler type to deliver a substantially accurate dose to a patient as measured using an inhaler training device 10 as a reference standard to guide the user's inhalation maneuver. Therefore, during an inhalation, a user can visually compare his/her inhalation maneuver to the baseline standard. It is possible to omit the medicament form the inhaler during training of the user so that the medicament is not wasted on failed inhalation maneuvers. In this manner, the user can alter his/her inhalation effort to conform to the requirements of the standard when the drug is actually inhaled. The displayed data for each inhalation performed by a subject can be saved via second connection 76 to output 55, wherein the data can be stored or transferred accordingly. For example, output 55 can be in the form of a disc drive or flash drive or printer, or transmitted via email or text to a physician for review or further training as needed. In some embodiments, signals from an inhalation training device can be transmitted to the computer/PDA/mobile/tablet and signals from the computer/PDA/mobile/tablet can be received by the inhalation training device, thereby establishing a two way communication between the two components. For instance, a user can input into computer 57 certain information such as patient number, dose strength, comments on condition, etc. In this and other embodiments, sensor 52 is a digital sensor or a sensor that can produce a digital output. It can be an accelerometer, a Doppler sensor, a luxometer or a laser and signal detected can be transmitted directly to the on-board microprocessor and analyzed, processed and transmitted thereafter. Signal information in the microprocessor can be analyzed and processed using algorithms, which converts the data, for example, into a pressure versus time curve using a graphical interface that can be displayed. Signals from sensor 52 can carry information relating to flow, pressure differential, and the like that is different from the signal in sensor 51 if both are employed.

Further, other on-board devices 78 can send data to and receive data from microprocessor 70 through one or more cable 79. For example, other on-board devices can include digital output sensors, temperature sensors, light emitting diodes (LEDs), sound warning devices, and other on-board sensors. These on-board devices can be used to output pass/fail criteria of an inhalation maneuver with an LED light or audible indicator of such pass/fail. Temperature, humidity or other environmental data can be used to determine the environment in which the inhaler was used.

For sensor 51 output, following the signal amplification, amplified signal 65 alternatively can be directly sent to computer 506 via wireless communicator 72 and the computer can implement the analog to digital conversion and other required analysis steps.

FIG. 10 illustrates a block diagram of an embodiment of a detection and monitoring system disclosed in FIG. 8 with integrated display. Inhalation detecting and sensing apparatus 82 comprises an inhaler accessory apparatus comprising an on-board electronic system with a built-in display 84, a microprocessor 86; an analog sensor 88 and a digital sensor 89. The system in use is actuated by the user 90 depressing actuator button 19 with power supplied by battery 92. When the user inhales through an inhaler adapted with inhaler accessory apparatus comprising the on-board electronic system 82, one or more of the sensors 88, 89 generates a signal which is transmitted to the microprocessor 86. For example, an acoustic sensor or a microphone 88 can be used to generate an electrical signal 94 which is transmitted to a signal conditioner 96 to remove excess noise and thereafter, the electrical signals are sent to a bandwidth limiter 98 to reduce the frequency of the signal to a desired range to reduce the data needing to be analyzed and the signal then is transmitted to a signal amplifier 95, wherein in the signal is amplified and transmitted to an analog to digital converter 97 and the digital signal is communicated to an on-board microprocessor 86 for analysis and converting the information to a graph and sent to display 84 for visualizing. Sensor 89 which is a digital sensor can be used alternatively or in conjunction with sensor 88 to detect signals and generate a set of signals for transmission to microprocessor 86, wherein the signal is analyzed, stored and sent to display 82 as well. Other devices, including other sensors 99 can also be included to detect other parameters of the inhaler or the system.

FIG. 11 illustrates a block diagram of an embodiment of a detection and monitoring system 100 disclosed herein with visual indicators of performance rather than an integrated display showing the operational parts of the system. In this embodiment, two sensors are provided, analog sensor 101 and digital sensor 102. Upon activation of the system 100 powered by battery 103, a patient/user 105 inhales generating signals such as sound from airflow traveling through the inhaler conduits. Sensors 101, 102 are activated and establish signals from the inhaler and relay the signals downstream; sensor 102 can be a Doppler which can receive, for example, output signals from airflow detection can be either analog or digital. If output signals from sensor 102 are digital, they are transmitted directly to microprocessor 110 for analysis and processing of the incoming information. Concurrently, sensor 101 generates electrical signals, which are sensed in the inhaler, through to signal conditioner 106 to remove excess noise, then the conditioned signals are transmitted to bandwidth limiter 108 for selecting the data to be analyzed. The limited signals are then transmitted to a signal amplifier 109 wherein the signal is amplified and relayed to analog to digital converter 112. The signal received is then converted to a digital signal and transmitted to the on-board microprocessor for analysis and processing with an algorithm which converts the data into, for example, a visual or light signal and can be displayed as a visual indicator, such as a green light or red light to indicate if the patient's inhalation effort "passed," meaning an inhalation with appropriate effort to deliver the dry powder dose, or if the patient's inhalation effort was insufficient to deliver a dry powder dose from the inhaler tested. In this embodiment, other on-board devices 115 can be integrated in the circuit, such as other sensors, or signal conditioners, amplifiers and A/D converters depending in the types of sensors use. For example, an inhaler accessory apparatus can have two or more analog sensors and therefore, the electrical signals must go through an A/D converter prior to be transmitted to a microprocessor for analysis and processing of the information. In alternate embodiments, digital sensors can be used which output signals can directly communicate with the microprocessor.

In other embodiments, an inhaler accessory apparatus can have one or more than one sensor, including a temperature sensor, laser beam, Doppler sensor, luxometer, color sensors, text recognition, RFID, optical character recognition, optical identification, pattern recognition, which output signal can be, for example, if not a digital signal output, an analog signal output that must be converted into digital signals for further analysis and processing once they reach the microprocessor. These sensors are preferably included on the inhaler accessory apparatus to identify what medicament is loaded in the inhaler to be administered and what cartridge type or dosage of such medicament is loaded in the inhaler.

Figure 12:
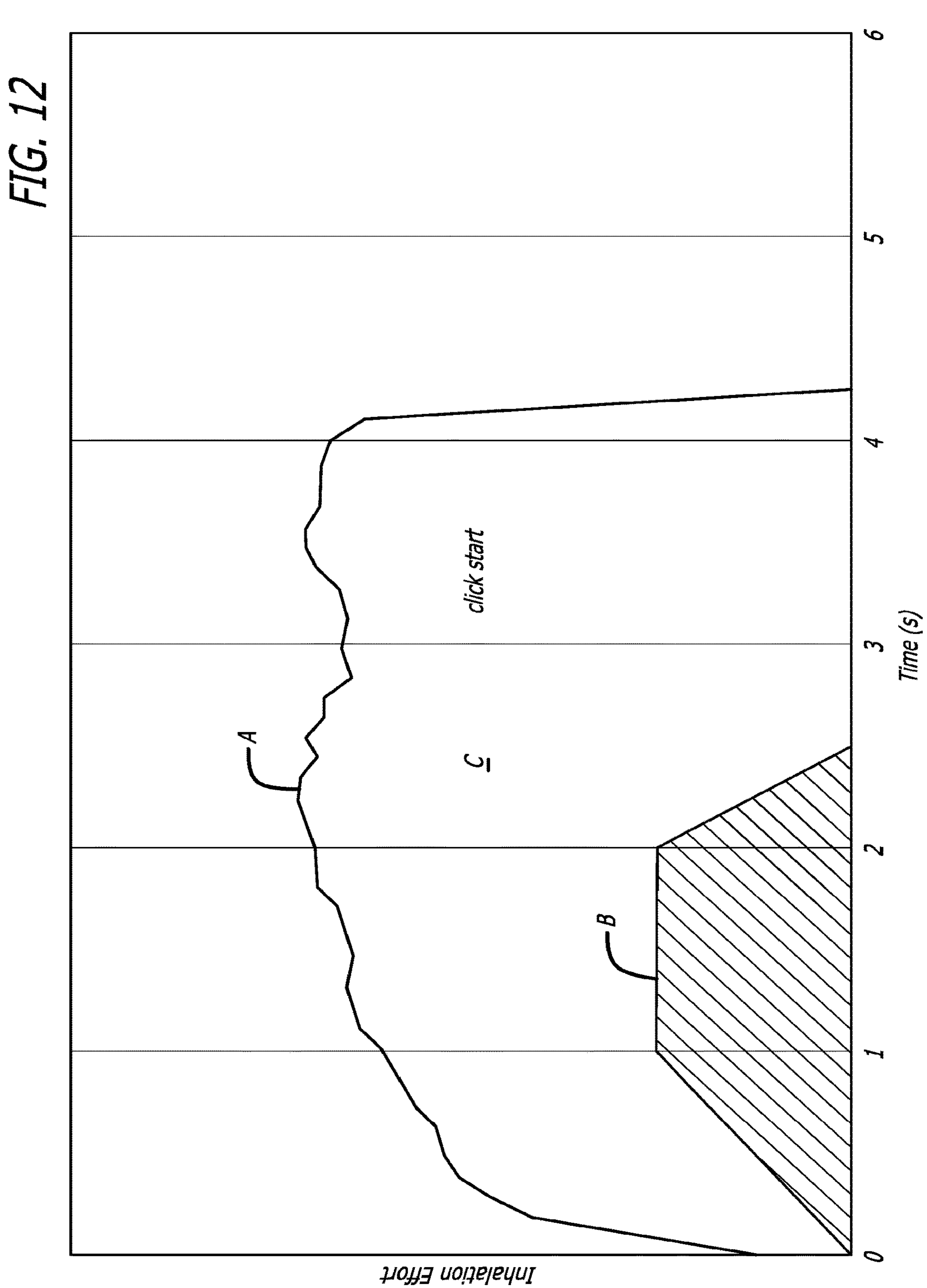
FIG. 12 graphically illustrates an inhalation maneuver performed by a subject coached to take a breath for the purposes of monitoring inhalation effectiveness for dosing.

FIG. 12 shows a screen shot of a tablet/computer/PDA/phone 57 of processing system 56 in FIG. 9. The computer 57 is used to communicate remotely with the inhaler accessory apparatus 54 using Bluetooth® or another remote wireless technology, wherein the inhaler accessory apparatus 54 is adapted to an inhaler and the subject is asked to inhale through the mouthpiece of the inhaler when the system is activated. The resultant graph on the screen as shown in FIG. 12 is plotted in response to the inhalation maneuver as inhalation effort on the y-axis, taking into account sensor (e.g., pressure) measurements and flow versus time in seconds on the x-axis. The subject's inhalation effort is represented by the curve A above the trapezoid B figure at the base of the graph. The trapezoid B outer limits (i.e. above the area) is interpreted as indicating the threshold or minimum inhalation effort a subject must exert to be able to effectively and consistently inhale a powder dose from the inhaler used to empty the contents of the powder in the inhaler in taking a dose. An identification sensor, such as those described herein located in the inhaler accessory apparatus, detects and transmits data associated with the inhaler, medicament type, dosage, lot, expiration, etc. Such data is processed to identify the corresponding threshold data for user indication. The trapezoid also indicates the minimal characteristic criteria the inhaler exhibits or effort the inhaler requires to deliver a dry powder dose consistently, which delivery is greater than 90% to the patient. FIG. 12 graphically illustrates the example display of an inhalation maneuver performed by a subject who was asked to inhale deeply and is allowed to see the display screen on a tablet while performing the inhalation. As can be seen by such curve, the subject performed entirely within acceptable values in region A.

Additionally, FIG. 12 depicts a baseline inhalation performance standard for inhaler accessory apparatus 10 and the medicament identification. The user detected curve A can be bordered by a warning region just above region B and an acceptable or preferred region C above the warning region. Regions B and C and the warning region can be provided in different colors to facilitate discernment of regions in monitoring an individual's performance during an inhalation. Region B can be, for example, depicted in red, indicating that the inhalation maneuver did not meet the baseline requirement; therefore, the delivery system would not be optimal to deliver a medicament effectively. The warning region can be depicted in yellow indicating a warning that the inhalation maneuver is nearing the unacceptable performance effort. Preferred region C can be depicted in green indicating that the inhalation performance is in the acceptable efforts to effectively deliver a medicament. This displayed information detected from one or more sensors in the apparatus can be used by a clinician, physician or user to determine whether proper dosing occurred or it can be used to train the user on how much effort is needed to ensure proper dosing of the medicament.

Figure 13:
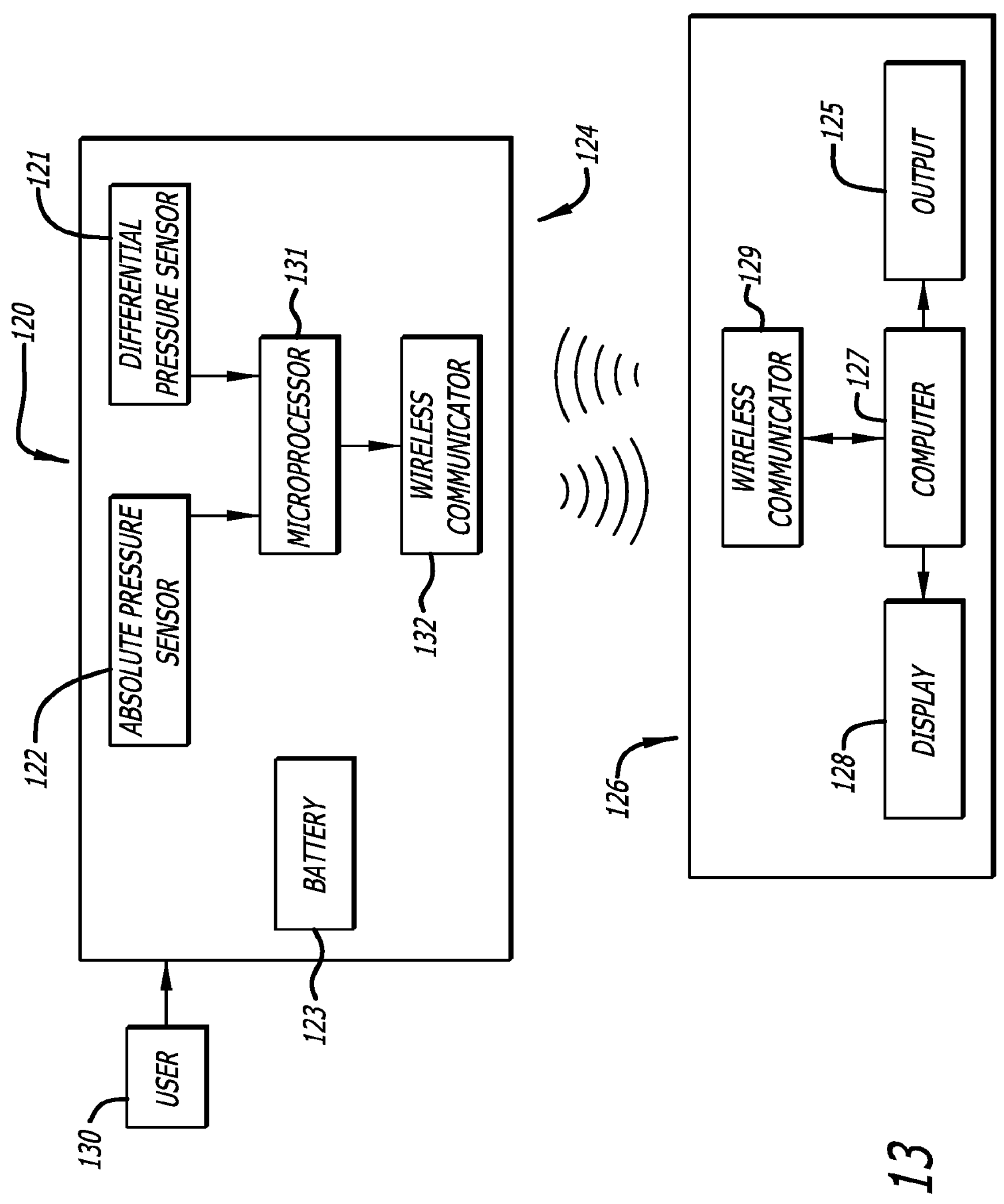
FIG. 13 illustrates a block diagram of an embodiment of a wireless detection and monitoring system disclosed herein where the inhaler accessory apparatus includes pressure sensors.
Figures 14, 15:
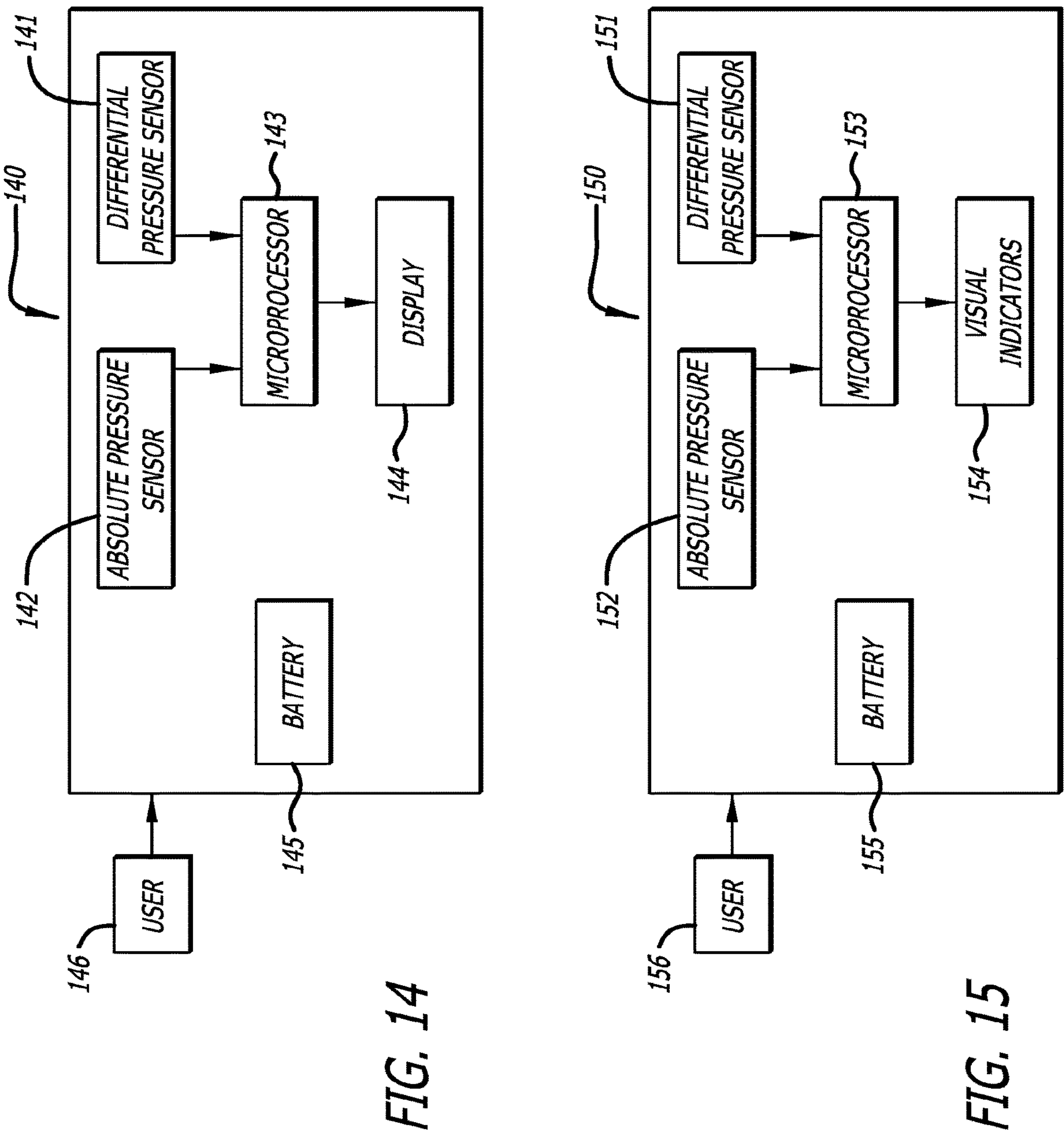
FIG. 14 illustrates a block diagram of an embodiment of a detection and monitoring system disclosed herein where the inhaler accessory apparatus includes pressure sensors and a display.
FIG. 15 illustrates a block diagram of another embodiment of a detection and monitoring system disclosed herein where the inhaler accessory apparatus includes pressure sensors and visual indicators.

FIGS. 13, 14 and 15 illustrate various operational embodiments of the inhalation detection and monitoring system shown in FIGS. 1-8. FIG. 13 illustrates a block diagram of an overall embodiment of a wireless detection and monitoring system as disclosed herein. In FIG. 13, system 120 comprises two components, inhaler training device or accessory apparatus 124 and processing system 126. Processing system 126 can include a PDA, mobile telephone, or computer 127, display 128, wireless communicator 129 and output 125 which can be in the form of digital storage, a web interface, a print out or the like. In this example embodiment, a user can activate inhaler training device or apparatus 120 by depressing a power button, for example button 19 on training device 10, with processing system 126 also activated. When the software program integrated with computer 127 is initiated, a start signal appears on display 128. In this embodiment, the accessory apparatus 120 comprises an electronic board having preferably two pressure sensors 121 and 122 placed so that they are in close proximity to the inhaler airflow conduits so as to be able to detect the differential pressure from the inhaler and the absolute pressure of the environment from the inhaler 14 when apparatus 10, 12 is actuated or turned on by depressing actuator button 19, 26 which is connected to a power source, such as battery 123 that also provides power to the system. With the system activated, a user's inhalation 130 generates a pressure drop in inhaler training device 120, which is measured by sensor 121. Absolute pressure sensor 122 provides a data or signal used to correct the differential pressure reading for atmospheric conditions.

In this embodiment, sensors 121 and 122 are pressure sensors that are digital. Signals generated by sensors 121 and 122 are then transmitted to microprocessor 131 and into wireless communicator 132. A software program built into/programmed into microprocessor 131 or computer 127 converts signals generated by sensors 121 and 122 to a (corrected) pressure value which can be displayed graphically in display 58, which can be a screen comprising LED, OLED, LCD, touch screen, or other interactive display.

FIG. 14 illustrates a block diagram of an embodiment of a detection and monitoring system disclosed herein. The inhalation detecting and sensing apparatus comprises an inhaler accessory apparatus comprising an on-board electronic system 140 with a built-in or integrated display 144, a microprocessor 143, and pressure sensors 141 and 142. The system in use is actuated by user 146 with power supplied by battery 145. With the system activated, a user's inhalation 146 generates a pressure drop in inhaler training device 140, which is measured by sensor 141. Absolute pressure sensor 142 provides a data or signal used to correct the differential pressure reading for atmospheric conditions. In this embodiment, sensors 141 and 142 are pressure sensors that are digital. If analog sensors are implemented, additional circuit elements would be necessary for conditioning, filtering, amplifying and/or converting the signals as discussed hereinabove. Signals generated by pressure sensors 141 and 142 are then transmitted to microprocessor 143. A software program built into/programmed into microprocessor 143 converts signals generated by sensors 141 and 142 to a (corrected) pressure value which can be displayed graphically in display 144, which can be a screen comprising LED, OLED, LCD, touch screen, or other interactive display.

FIG. 15 illustrates a block diagram of an embodiment of a detection and monitoring system disclosed herein. Inhalation detecting and sensing apparatus comprises an inhaler accessory apparatus comprising an on-board electronic system 150 with integrated visual indicators 154, a microprocessor 153; and pressure sensors 151 and 152. The system in use is actuated by user 156 with power supplied by battery 155. With the system activated, a user's inhalation 156 generates a pressure drop in inhaler training device 150, which is measured by sensor 151. Absolute pressure sensor 152 provides a data or signal used to correct the differential pressure reading for atmospheric conditions. In this embodiment, sensors 151 and 152 are pressure sensors that are digital. If analog sensors are implemented, additional circuit elements would be necessary for conditioning, filtering, amplifying and/or converting the signals as discussed hereinabove. Signals generated by pressure sensors 151 and 152 are then transmitted to microprocessor 153. A software program built into/programmed into microprocessor 153 converts signals generated by sensors 151 and 152 to a (corrected) pressure value which can be used to activate visual indicators 154 which can be used to indicate a correct inhalation or other information.

Figure 16:
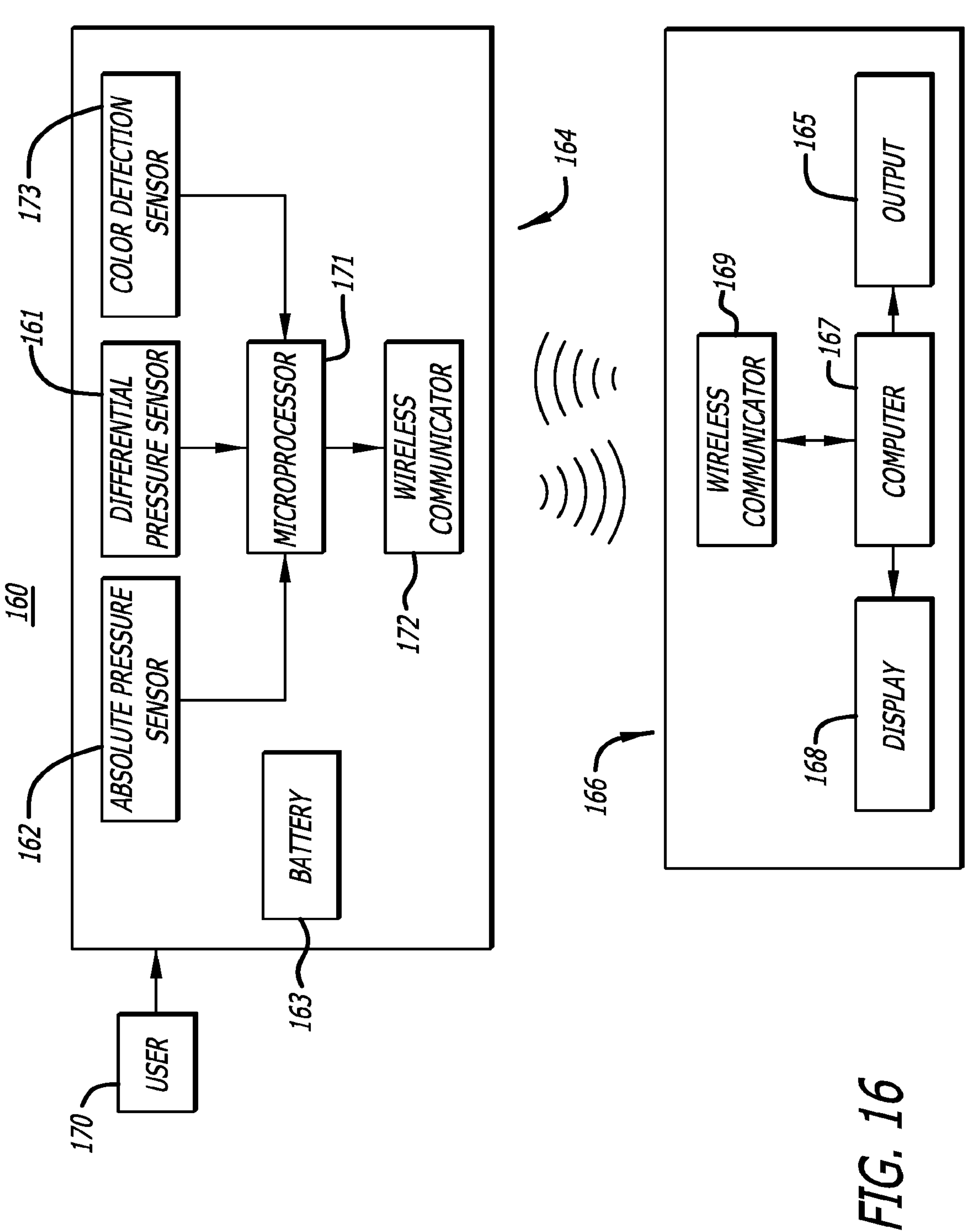
FIG. 16 illustrates a block diagram of an embodiment of a wireless detection and monitoring system disclosed herein where the inhaler accessory apparatus includes a color detection sensor and pressure sensors.

FIG. 16 further illustrates a block diagram for, for example, an inhaler training device, such as apparatus 10, showing further various operational component parts. In FIG. 16, system 160 comprises two components, inhaler training device or accessory apparatus 164 and processing system 166. Processing system 166 includes a tablet, PDA, mobile telephone, or computer 167, display 168, wireless communicator 169 and output 165 which can be in the form of digital storage, a web interface, a print out or the like. In this example embodiment, a user can activate inhaler training device 160 by depressing a power button, for example button 19 on training device 10, with processing system 160 also activated. When the software program integrated with computer 167 is initiated, a start signal appears on display 168. With the system activated, a user's inhalation 170 generates a pressure drop in inhaler training device 160, which is measured by sensor 161. In this embodiment, sensors 161 and 162 are pressure sensors that are digital. Signals generated by color detection sensor 173 and pressure sensors 161 and 162 are then transmitted to microprocessor 171 and into wireless communicator 172. A software program built into/programmed into microprocessor 171 or computer 167 converts signals generated by color detection sensor 173 and sensors 161 and 162 to a cartridge information value and a pressure value, respectively, which can be displayed graphically in display 168, which can be a screen comprising LED, OLED, LCD, touch screen, or other interactive display. The cartridge information value can be used to provide the limits to powder dose efficacy and plot the trapezoid B or other threshold indication on the graph. As referenced in earlier embodiments, in addition to color detection devices, other devices on the apparatus board can include laser, RFID, pattern or text/character readers or sensors with connections to the microprocessor to otherwise identify the inhaler, drug or cartridge/packaging of the substance/drug. These sensors/readers function to provide data to the system and microprocessor relating to medicament, substance, packaging, dosing, inhaler, etc. so that the corresponding data can be retrieved from storage and used as data points on any visual, audible or other indicator including a graph presented to the user. As an example, certain cartridges or other packaging can be color coded or include encrypted or encoded text, RFID indicating specific information about them including lot, expiration date, dosages, etc. A reader or sensor that can detect the code and send the corresponding data to the microprocessor for use in calculations, identified actions, and data presentation. Perhaps a certain color package indicates the use of a drug dose that requires greater effort to inhale properly. In this case, the accessory device or system will identify the proper color through the sensor/reader and use the proper data for instruction to the user.

Figures 17, 18:
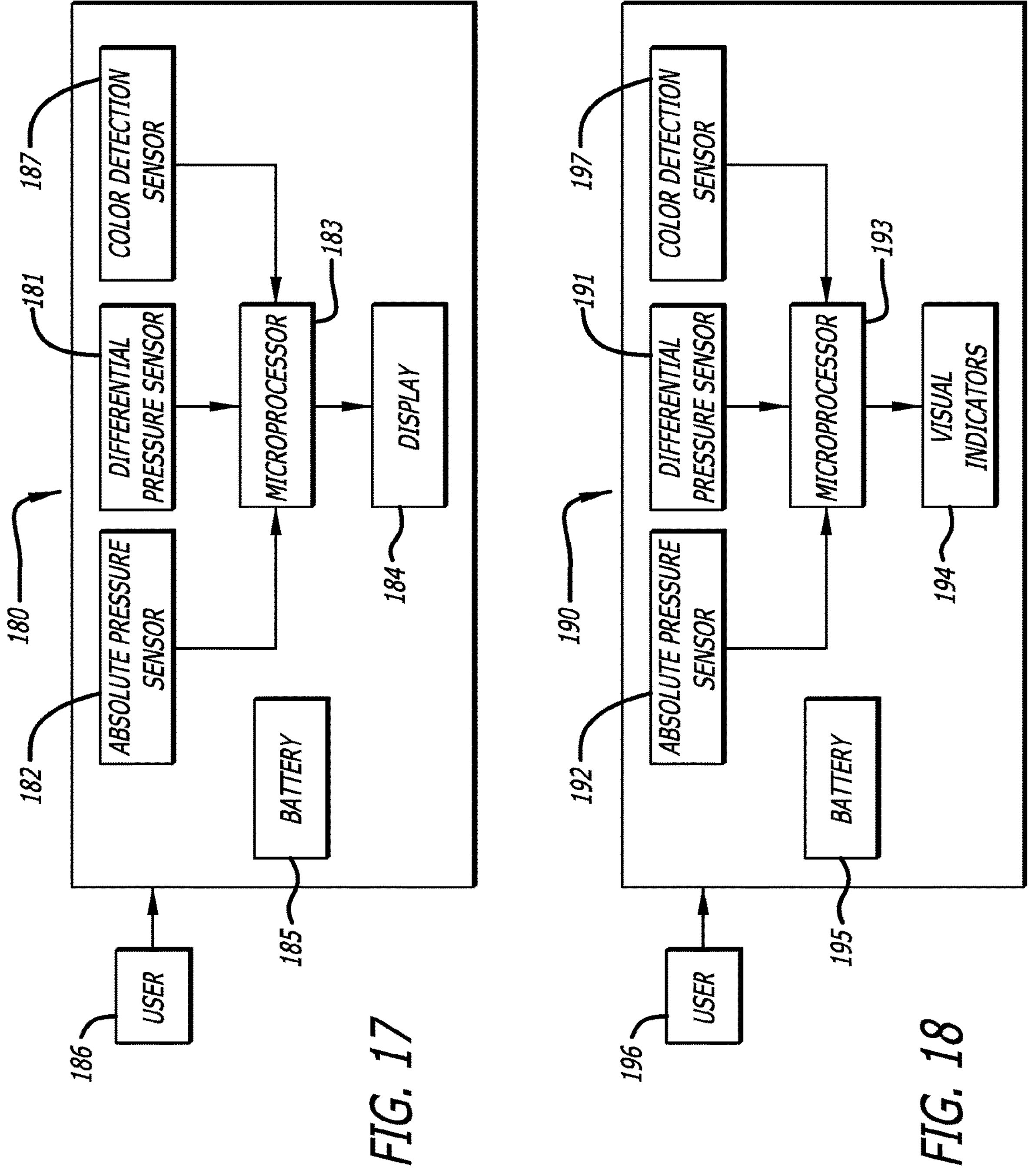
FIG. 17 illustrates a block diagram of an embodiment of a detection and monitoring system disclosed herein where the inhaler accessory apparatus includes a color detection sensor and a display.
FIG. 18 illustrates a block diagram of another embodiment of a detection and monitoring system disclosed herein where the inhaler accessory apparatus includes a color detection sensor and visual indicators.

FIG. 17 illustrates a block diagram of an embodiment of a detection and monitoring system disclosed herein. Inhalation detecting and sensing apparatus 180 comprises an inhaler accessory apparatus comprising an on-board electronic system with a built-in or integrated display 184, a microprocessor 183, color detection sensor 187 and pressure sensors 181 (differential) and 182 (absolute). The system in use is actuated by user 186 with power supplied by battery 185. With the system activated, a user's inhalation 186 generates a pressure drop in inhaler accessory apparatus, which is measured by sensor 181. Absolute pressure sensor 182 provides a data or signal used to correct the differential pressure reading for atmospheric conditions. In this embodiment, sensors 181 and 182 are pressure sensors that are digital. Signals generated by color detection sensor 187 and pressure sensors 181 and 182 are then transmitted to microprocessor 183. A software program built into/programmed into microprocessor 183 converts signals generated color detection sensor 187 and sensors 181 and 182 to a cartridge information value and a (corrected) pressure value which can be displayed graphically in display 184, which can be a screen comprising LED, OLED, LCD, touch screen, or other interactive display.

FIG. 18 illustrates a block diagram of an embodiment of a detection and monitoring system disclosed herein. Inhalation detecting and sensing apparatus 190 comprises an inhaler accessory apparatus comprising an on-board electronic system with integrated visual indicators 194, a microprocessor 193, color detection sensor 197 and pressure sensors 191 (differential) and 192 (absolute). The system in use is actuated by user 196 with power supplied by battery 195. With the system activated, a user's inhalation 196 generates a pressure drop in inhaler accessory apparatus, which is measured by sensor 191. Absolute pressure sensor 192 provides a data or signal used to correct the differential pressure reading for atmospheric conditions. In this embodiment, sensors 191 and 192 are pressure sensors that are digital. Signals generated by color detection sensor 197 and pressure sensors 191 and 192 are then transmitted to microprocessor 193. A software program built into/programmed into microprocessor 193 converts signals generated color detection sensor 197 and sensors 191 and 192 to a cartridge information value and a (corrected) pressure value, respectively, which can be used to activate visual indicators 194 which can be used to indicate a correct inhalation or other information.

Figure 19:
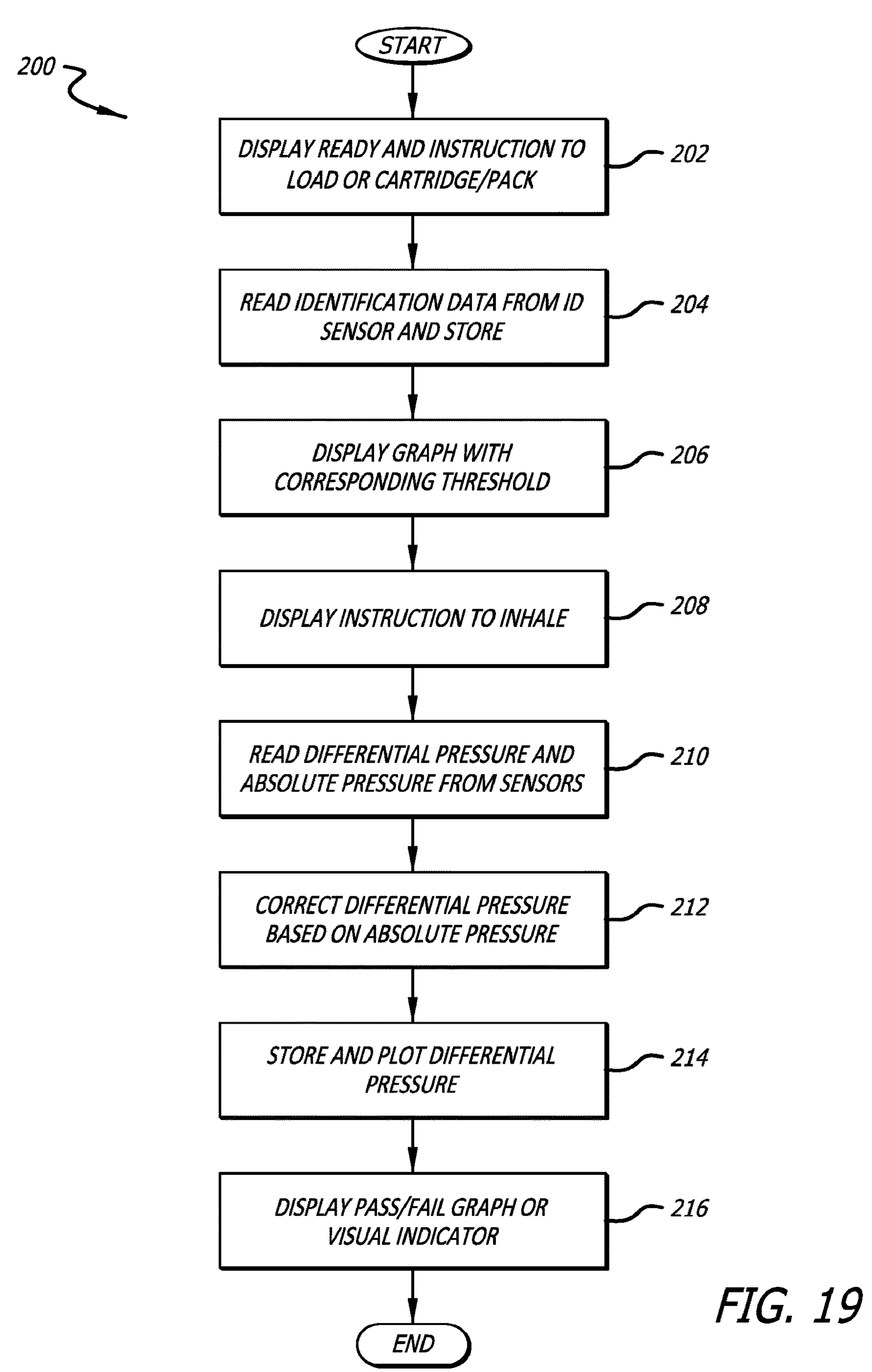
FIG. 19 illustrates a method of training or monitoring inhalation in a user with the system of FIG. 16

FIG. 19 illustrates a flowchart diagram of an embodiment of a method 200 of detecting, monitoring and training an inhalation subject according to the system disclosed in FIG. 16. When a user is to use the apparatus and system, he or she actuates the system by depressing the actuator on the inhaler accessory apparatus to start. Next in step 202, the wireless communicator of the inhaler accessory apparatus links using, for example, standard Bluetooth® technology, to the user's smart phone and an application on the phone displays a ready message and instructs the user to load the related inhaler with which the apparatus is engaged or provide a cartridge or other disposable package of the substance to be inhaled into the inhaler. In step 204, after such loading occurs, the identification sensor, in this case a color detection sensor 173 determines the color of the cartridge and stores it in data storage on the accessory apparatus board or wirelessly transmits it via Bluetooth® to the processing system 166 (phone) for storage. In step 206, the application displays a graph with the corresponding threshold data points provided based on the color detection. The user is next instructed to inhale in step 208 through use of some visual, audible or screen based message. In step 210, during an inhalation maneuver, the sensors 161, 162 read the pressure drop. Next, step 212 shows a correction step taken by the system based on the atmospheric conditions which occurs substantially simultaneously with step 210 or just thereafter. In either case, the pressure data is stored as above and preferably plotted on a graph in step 214. In step 216, the inhalation maneuver graph is displayed to the user with along with the threshold graph showing either a pass (successful inhalation) or a fail (unsuccessful inhalation). At that time, the user can depress the actuator to end the program and the data remains stored in the output 165 for future use.

In some example embodiments disclosed herein, one or more key parameters can define an acceptable inhalation maneuver, including, total inhalation time, peak inspiratory pressure, time to peak inspiratory pressure and average pressure from peak to about 75% of the total inhalation time. In certain embodiments, the total inhalation time can be greater than 5 seconds, the peak differential inspiratory pressure can be greater than about 6 kPa, time to peak inspiratory pressure can be less than about 1.1 seconds and the average pressure from peak differential inhalation to 75% of total inhalation time is about 4 kPa. These values are representative of values for an inhalation monitoring system 10, 12 and apparatus 18 and related algorithms/programs used for training and monitoring. They can be modified for alternate inhaler training devices, depending on the performance parameters required for optimal delivery of the medicament of the inhaler, including resistance.

In another example embodiment, a dry powder inhaler can be provided with a sensing and/or monitoring device which can monitor and/or sense signals generated by or within a dry powder inhaler during an inhalation maneuver by a patient. Dry powder inhalers can be provided with a sensor device either integrated into the device or attached thereto. Alternatively, in an example embodiment, accessory apparatus 18, 24 can be provided as an integral part of dry powder inhaler on mouthpiece or housing as desired.

In alternate embodiments, the inhaler accessory device 18, 24 is a mountable/detachable sensing and monitoring device that can disengage from the inhaler and is provided in the form of a jacket or cap, wherein detachable sensing and monitoring device can be provided as a detachable part that can adapt to a dry powder inhaler, in particular, for wireless communication so that the subject using the device has easier access and movement. In this embodiment, the jacket is manufactured as a separate, detachable device comprising on-board electronics including one or more microprocessors, wireless transceivers, A/D converters, sensors (such as a pressure sensor or a microphone) which can detect signals and being capable of storing, transmitting or displaying the signals.

When using acoustic sensors, sound waves emanating from the inhaler in use with or without a dry powder are detected by the microphone and the signals can be analyzed and correlated to time of powder discharge in the presence of a dry powder, airflow rate, end of powder discharge during an inhalation maneuver, temperature within the inhaler pathway, and the like, depending on the type of sensor used. For example, an increase in sound can be correlated to an increase in flow rate through the device, and/or powder particles collisions in the air stream during delivery.

A sensor such as a microphone, as a result of its small size, can be placed anywhere in the inhaler. In embodiments wherein the sensor is a pressure transducer, the sensor can be placed within an air conduit passing through one of the inhaler compartments. The sensors can be provided, for example, in an air conduit on or within the inhaler or provided as a separate, detachable part as an accessory to the inhaler with a shape or configuration that can be adapted to the inhaler to which is to be adapted, and can include a cap, a jacket, sleeve or a saddle-like configuration that can be adapted or mounted to the inhaler.

For the detachable embodiments, the sensing and monitoring accessory apparatus is easy and inexpensive to manufacture and can be made from plastics, and works well with high resistance dry powder inhalers. In some embodiments, the sensor can be any sensor, for example, a thermocouple wire, a pressure transducer, an analog sensor, a microphone, an optical sensor, a gas sensor, or any sensor that can detect signals generated within an inhaler. The sensors described herein can be adapted to communicate or transmit signals with a transceiver device or the signals can be transmitted or stored using wire connection to an analog to digital converter prior to transmitting this signals to a microprocessor.

Alternatively, an analog to digital converter is provided within the inhaler device and resulting digital data is transferred out of the device directly. The signals provided by the sensors described herein can be in several forms including sound generated in an inhaler by airflow passing through the air conduits and/or powder particles collisions entrained in the air flow pathway and pressure drops detected proximate to the airflow pathway due to the inhalation maneuver. Signals generated from the inhaler can be detected by the sensors and stored, transmitted or displayed. Other types of signals that can be detected by the system are text, color, encryptions or codes, which can be detected by light beams, laser beams, and Doppler sensors which are, preferably, integrated into the electronic board. Data can be generated from the signals and qualitatively and/or quantitatively analyzed. In this manner, measurements can be made including time of dose release, amount of dose, type of dose, time of dose, and the like. Further, these signals, for example, can be associated with identification of the patient, the medicament type and dosage, the inhaler or otherwise and can be used to model the data requirements for proper inhalation and facilitate training of the inhaler user.

In one example embodiment, a sensing and monitoring system for an inhaler includes an accessory apparatus structurally configured to be adapted to an inhaler; a sensor, a microprocessor, an optional analog to digital converter; and a data storage medium. The data storage medium includes a disc drive, a DVD, CD-ROM, a server, a flash card or drive, memory card, and the like and includes a set of machine-readable instructions that are executable by a microprocessor or other processing device to implement an algorithm. The algorithm, when run, initiates the steps of generating a logical sub-system generation number derived from detected signals; saving the logical sub-system generation number to a data track within a logical sub-system, wherein the logical sub-system generation number and a cluster generation number in the processing device are compared; and storing and/or displaying information from the algorithm as the results from an inhalation maneuver.

In a particular embodiment, the inhaler accessory apparatus is useful for dry powder inhalers, in particular, with a unit dose cartridge, and a drug delivery formulation comprising, for example, diketopiperazine, in particular, fumaryl diketopiperazine and an active ingredient such as peptides and proteins, including, endocrine hormones, including, parathyroid hormone, insulin, oxyntomodulin and glucagon-like peptide 1; neurotransmitters, including cannabinoids, 5-hydroxytryptamine, dopaminergic, prostacyclin, opioid agonists and antagonists. In some embodiments, the active ingredient in the formulations comprises one or more of the active agents, which include, but are not limited to treprostinil, salmeterol, epinephrine, tacrolimus, vancomycin, linezolid, filgastrin, fentanyl, cannabidiols, THC, palonosetron, amphotericin B, phosphodiesterase inhibitors, including, PDE5 inhibitors such as sildenafil, avanafil, verdenafil and tadalafil; prostaglandins, prostacyclin, neurotransmitter agonists, neurotransmitter antagonists, including anti-nociceptive agents, opioid analgesics such as delta opioid agonists and antagonists, kappa opioid receptor agonists and antagonists, mu opioid receptor agonist and antagonists.

Example 1

Using an Integrated Training Device

A 60 year old Type I diabetic is instructed to receive inhaled insulin for prandial treatment therapy, which is provided from a dry powder inhalation system, because she has an elevated hemoglobin A1c and is considered out of control. The patient uses an insulin pump for basal insulin. The patient is trained for wireless inhalation using a device as illustrated in FIG. 1 with a removable inhalation accessory apparatus as shown in FIGS. 3-5. The patient is given the device and asked to take a deep rapid breath in using the training device which may or may not include the medicament.

Pressure sensors on the inhalation apparatus are used to detect pressure drop during the inhalation and the data is wirelessly transmitted to a Bluetooth® enabled tablet with an associated application. Color detection sensors detect the cartridge (with substance or empty) color and the data is used to identify the threshold region for minimal inhalation pressure. The data is collected on the tablet having a programmed application which can read radio signals from the device and the patient is able to view the data in real-time on a display screen. The patient's first inhalation attempt is too slow and is indicated on-screen as entering a red "unacceptable region" (B region) of FIG. 12. The patient is instructed to take another rapid breath in that is slightly faster and deeper than the previous attempt. Upon completion of the inhalation, the graph illustrates that the patient's inhalation maneuver was acceptable and entirely in the acceptable region of the graph (C region) of FIG. 12. Upon being comfortable with the training, the patient is clear for use of a similar inhaler device with the medicament loaded therein.

The patient is prescribed a dry powder inhaler similar to the type that illustrated in FIG. 1 and cartridges filled with an inhalable insulin of various doses for treatment of the patient's diabetes. Six months after prescribing the inhaled insulin, the patient's diabetes is diagnosed as under control.

Example 2

Using an Attachable Training Device

A 59 year old Type II diabetic is instructed to receive inhaled insulin from a dry powder inhalation system. The patient has requested the inhalation system for convenience reasons. The patient is trained for wireless inhalation using a device as illustrated in FIG. 1. The patient is given the device of FIG. 1 equipped with an attachable inhaler apparatus similar to that of FIG. 3-5 and asked to take a deep rapid breath in using the training device.

The pressure and color identification data is collected on a mobile phone and the patient is able to view the data in real-time on a display screen. The patient's first attempt is acceptable as indicated by the threshold vs. inhalation data graphed or otherwise visually indicated as a result of the software. Upon being comfortable with the training, the patient is clear for use of the device.

The patient attachable sensor is removed from the dry powder inhaler. The patient is given the dry powder inhaler and cartridges filled with inhalable insulin for treatment of the patient's diabetes. Six months after prescribing the inhaled insulin, the patient's diabetes is diagnosed as under control and the patient comments on the great convenience of the device.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of this disclosure.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosed embodiments are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosed embodiments (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosed embodiments and does not pose a limitation on the scope of the embodiments otherwise claimed. No language in the specification should be construed as indicating any non-claimed element essential to the practice of disclosed and contemplated embodiments.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the authors of this disclosure for carrying the disclosed and contemplated embodiments. Of course, variations on these described embodiments will become apparent to those of ordinary skill in the art upon reading the foregoing description. The authors expect skilled artisans to employ such variations as appropriate, and the authors intend for the disclosed and contemplated embodiments to be practiced otherwise than specifically described herein. Accordingly, the presently disclosed and contemplated embodiments include all modifications and equivalents of the subject matter recited in the claims appended hereto as permitted by applicable law. Moreover, any combination of the above-described elements in all possible variations thereof is encompassed by this disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments disclosed and contemplated herein are illustrative of the principles of the conceived invention. Other modifications that may be employed are within the scope of this disclosure. Thus, by way of example, but not of limitation, alternative configurations may be utilized in accordance with the teachings herein. Accordingly, the disclosed embodiments are not limited to that precisely as shown and described.

We claim:

1. A method of monitoring and detecting data for dry powder inhaler user training, comprising:

displaying an instruction to load a medicament in the dry powder inhaler;

reading medicament data relating to medicament or inhaler information via a contactless identification sensor comprising a laser beam, a Doppler sensor, an infrared sensor or another sensing beam configured to detect information encrypted or coded by color in areas or parts of the dry powder inhaler, an inhaler cartridge or another medicament package;

identifying absolute pressure data before inhalation by a user via an absolute pressure sensor configured to obtain an absolute pressure;

adjusting for atmospheric conditions;

displaying instruction to begin an inhalation maneuver;

obtaining pressure differential data and flow data during the inhalation by the user via a differential pressure sensor detecting a pressure drop and a flow sensor detecting flow measured in an inhaler conduit of the dry powder inhaler and having been adjusted by the absolute pressure data for the atmospheric conditions;

computing a threshold of a minimum inhalation effort the user must exert to effectively inhale the medicament by relating the medicament data and the pressure differential data;

determining whether the user passed or failed the inhalation maneuver based on the computed threshold; and displaying the inhalation effort as a positive inhalation effort vs. time curve along with the threshold corresponding to the medicament data, the inhalation effort accounting for the pressure differential data adjusted by the absolute pressure data and flow data.

2. The method of claim 1, further comprising a step of transmitting an indication of whether a user inhalation profile met, failed to meet, or exceeded the computed threshold.

3. The method of claim 2, wherein the transmitting step comprises transmitting for display on a remote processing system such as a smart phone, tablet, computer or other wireless radio enabled device.

4. The method of claim 3, wherein the transmitting step comprises transmitting the medicament data and the pressure differential data to the remote processing system via wireless transmission.

5. The method of claim 4, further providing an application configured for the remote processing system to display the inhalation effort vs. time curve along with the threshold corresponding to the medicament data.

6. The method of claim 1, wherein the dry powder inhaler comprises a cartridge and a dry powder formulation.

7. The method of claim 6, wherein the dry powder formulation comprises a diketopiperazine and at least one active ingredient.

8. The method of claim 5, further providing the application configured to store the medicament data and pressure differential data.

9. A method of monitoring and detecting use of a dry powder inhaler, comprising:

providing an apparatus body configured for mounting onto or in connection with the dry powder inhaler, the body having at least two sensors comprising a contactless first sensor and a second sensor;

detecting activation of the apparatus body;

detecting an inhalation maneuver;

detecting information encrypted or coded by color in areas or parts of the dry powder inhaler, inhaler cartridge or other medicament package via the contactless first sensor comprising a laser beam, a Doppler sensor, infrared sensor or other sensing beam;

detecting signals generated from an inhaler conduit of the dry powder inhaler via the second sensor comprising an absolute pressure sensor, a third sensor comprising a flow sensor and a fourth sensor comprising a differential pressure sensor by obtaining absolute pressure data from the absolute pressure sensor;

obtaining flow data from the flow sensor;

obtaining differential pressure data from the differential pressure sensor configured for detecting a pressure drop measured in the inhaler conduit during the inhalation maneuver by a user, wherein the absolute pressure is used in conjunction with the differential pressure sensor to generate an adjusted pressure for atmospheric conditions before identifying the pressure drop;

generating a threshold profile by relating the detected information and adjusted pressure;

generating a pass or fail status upon completion of the inhalation maneuver based on computed threshold profile; and displaying a user inhalation profile as a positive inhalation effort vs. time curve along with the threshold profile corresponding to the medicament data, the user inhalation profile accounting for the pressure differential data adjusted by the absolute pressure data and flow data.

10. The method of claim 9, further comprising displaying instruction to begin inhalation.

11. The method of claim 9, wherein one or more of the generating steps are performed by a microprocessor comprised in the apparatus body.

12. The method of claim 9, further comprising generating the user inhalation profile based at least on the adjusted pressure and time.

13. The method of claim 12, further comprising determining resultant data of the inhalation maneuver based on comparison of the threshold profile to the user inhalation profile.

14. The method of claim 12, further comprising a step of transmitting the status of whether the user inhalation profile met, failed to meet, or exceeded the threshold profile for display.

15. The method of claim 14, wherein the transmitting step comprises transmitting for display on a remote processing system such as a smart phone, tablet, computer or other wireless radio enabled device.

16. The method of claim 15, wherein the transmitting step comprises transmitting the detected information and the pressure differential data to the remote processing system via wireless transmission.

17. The method of claim 16, further providing an application configured for the remote processing system to display the inhalation effort vs. time curve along with the threshold corresponding to the medicament data.

18. The method of claim 17, further providing the application configured to store the detected information and pressure differential data.

19. The method of claim 9, wherein the dry powder inhaler comprises a cartridge and a dry powder formulation.

20. The method of claim 19, wherein the dry powder formulation comprises a diketopiperazine and at least one active ingredient.

21. The method of claim 9, further comprising displaying an instruction to load a medicament into the dry powder inhaler.

22. The method of claim 4, wherein the transmitting step comprises transmitting to visual indicators that are pass/fail or green/red indicators in the form of light emitting diodes.

23. The method of claim 9, wherein the differential pressure sensor detects sound signals generated in the dry powder inhaler.

24. The method of claim 23, wherein the sound signals include an amplitude of the sound signal, a frequency of the sound signal, or combinations thereof.

25. The method of claim 24, wherein the differential pressure sensor is a microphone.

* * * * *